(12) United States Patent
Dussarrat et al.

(10) Patent No.: US 9,371,338 B2
(45) Date of Patent: Jun. 21, 2016

(54) ORGANOSILANE PRECURSORS FOR ALD/CVD SILICON-CONTAINING FILM APPLICATIONS

(71) Applicant: American Air Liquide, Inc., Fremont, CA (US)

(72) Inventors: Christian Dussarrat, Tokyo (JP); Glenn Kuchenbeiser, Newark, DE (US); Venkateswara R. Pallem, Hockessin, DE (US)

(73) Assignee: American Air Liquide, Inc., Fremont, CA (US)

(*) Notice: Subject to any disclaimer, the term of this patent is extended or adjusted under 35 U.S.C. 154(b) by 119 days.

(21) Appl. No.: 14/372,105

(22) PCT Filed: Jul. 19, 2013

(86) PCT No.: PCT/US2013/051244
§ 371 (c)(1),
(2) Date: Jul. 14, 2014

(87) PCT Pub. No.: WO2014/015232
PCT Pub. Date: Jan. 23, 2014

(65) Prior Publication Data
US 2015/0004317 A1    Jan. 1, 2015

Related U.S. Application Data

(60) Provisional application No. 61/674,103, filed on Jul. 20, 2012.

(51) Int. Cl.
*C23C 16/00*        (2006.01)
*C07F 7/02*         (2006.01)
(Continued)

(52) U.S. Cl.
CPC . *C07F 7/025* (2013.01); *B05D 1/60* (2013.01); *C23C 16/30* (2013.01); *C23C 16/345* (2013.01);
(Continued)

(58) Field of Classification Search
CPC .... C23C 16/401; C23C 16/44; C23C 16/402; C23C 16/36; C23C 16/345; C23C 16/30
USPC ......................................... 427/248.1, 255.29
See application file for complete search history.

(56) References Cited

U.S. PATENT DOCUMENTS 2,590,039 A    3/1952  Richter et al.
3,355,477 A    11/1967 Frye
(Continued)

FOREIGN PATENT DOCUMENTS

CN    104341447    2/2015
EP    1 310 500    5/2003
(Continued)

OTHER PUBLICATIONS

Weidenbruch, Manfred, A Stable Silylenoid and a Donor-Stabilized Chlorosilylene: Low-Coordinate Silicon Compounds—A Never-Ending Story?, Angewandte Chemie, 2006, 45, pp. 4241-4242.*
(Continued)

*Primary Examiner* — Kelly M Gambetta
(74) *Attorney, Agent, or Firm* — Patricia E. McQueeney

(57) ABSTRACT

Disclosed are Si-containing thin film forming precursors, methods of synthesizing the same, and methods of using the same to deposit silicon-containing films using vapor deposition processes for manufacturing semiconductors, photovoltaics, LCD-TFT, flat panel-type devices, refractory materials, or aeronautics.

19 Claims, 1 Drawing Sheet

(51) Int. Cl.

| | | |
|---|---|---|
| C23C 16/30 | (2006.01) | |
| C23C 16/34 | (2006.01) | |
| C23C 16/36 | (2006.01) | |
| C23C 16/40 | (2006.01) | |
| B05D 1/00 | (2006.01) | |
| H01L 21/02 | (2006.01) | |
| C23C 16/44 | (2006.01) | |

(52) U.S. Cl.
CPC .............. *C23C 16/36* (2013.01); *C23C 16/401* (2013.01); *C23C 16/402* (2013.01); *C23C 16/44* (2013.01); *H01L 21/0228* (2013.01); *H01L 21/02216* (2013.01); *H01L 21/02271* (2013.01); *H01L 21/02532* (2013.01)

(56) References Cited

U.S. PATENT DOCUMENTS

| | | | |
|---|---|---|---|
| 4,841,084 | A | 6/1989 | Corriu et al. |
| 5,394,269 | A | 2/1995 | Takamatsu et al. |
| 6,391,803 | B1 | 5/2002 | Kim et al. |
| 6,465,387 | B1 | 10/2002 | Pinnavaia et al. |
| 6,736,993 | B1 | 5/2004 | Xu et al. |
| 6,869,638 | B2 | 3/2005 | Baum et al. |
| 7,125,582 | B2 | 10/2006 | McSwiney et al. |
| 7,192,626 | B2 | 3/2007 | Dussarrat et al. |
| 7,332,618 | B2 | 2/2008 | Meiere |
| 7,482,286 | B2 | 1/2009 | Misra et al. |
| 7,875,312 | B2 | 1/2011 | Thridandam et al. |
| 8,129,555 | B2 | 3/2012 | Cheng et al. |
| 8,828,505 | B2 | 9/2014 | Thridandam et al. |
| 2006/0045986 | A1 | 3/2006 | Hichberg et al. |
| 2006/0258173 | A1 | 11/2006 | Xiao et al. |
| 2007/0160774 | A1 | 7/2007 | Tsukada et al. |
| 2007/0275166 | A1 | 11/2007 | Thridandam et al. |
| 2009/0302434 | A1 | 12/2009 | Pallem et al. |
| 2010/0112211 | A1 | 5/2010 | Xu et al. |
| 2010/0164057 | A1 | 7/2010 | Hunks et al. |
| 2010/0317150 | A1* | 12/2010 | Hunks .................. C07C 251/08 438/102 |
| 2011/0045676 | A1 | 2/2011 | Park et al. |
| 2011/0061733 | A1 | 3/2011 | Hurley et al. |
| 2011/0250354 | A1 | 10/2011 | Pallem et al. |
| 2012/0277457 | A1 | 11/2012 | Lehmann et al. |
| 2013/0022745 | A1 | 1/2013 | Dussarrat et al. |
| 2013/0078392 | A1 | 3/2013 | Xiao et al. |
| 2014/0031502 | A1* | 1/2014 | Qin ....................... C07F 5/003 526/126 |
| 2015/0087139 | A1 | 3/2015 | O'Neill et al. |

FOREIGN PATENT DOCUMENTS

| | | | | |
|---|---|---|---|---|
| EP | | 1563117 B1 * | 1/2010 | ............ C07C 257/14 |
| EP | | 2 154 141 | 2/2010 | |
| EP | | 2 392 691 | 12/2011 | |
| JP | | H06 132276 | 5/1994 | |
| JP | | H06 132284 | 5/1994 | |
| JP | | 2000 195801 | 7/2000 | |
| KR | | 2011 0009739 | 1/2011 | |
| KR | | 2012 0060843 | 6/2012 | |
| KR | 10 | 2012 0078909 | 7/2012 | |
| WO | | WO 01 79578 | 10/2001 | |
| WO | | WO 2006 097525 | 9/2006 | |
| WO | | WO 2006 136584 | 12/2006 | |
| WO | | WO 2009 087609 | 7/2009 | |
| WO | | WO 2011 103282 | 8/2011 | |
| WO | | WO 2011 123792 | 10/2011 | |
| WO | | WO 2012 176988 | 12/2012 | |

OTHER PUBLICATIONS

Baus, J.A. et al., "Neutral six-coordinate and cationic five-coordinate silicon(IV) complexes with two bidentate monoanionic N,S-pyridine-2-thiolato(—) ligands," Inorg. Chem, 2013, 52, 10664-10676.

Eilingsfeld, H. et al., "Synthesen mit Amidchloriden, III. Synthese und Reaktionen von Chlorformamidiniumchloriden," Chemische Berichte vol. 97, Issue 5, May 1964, 1232-1245.

Siddiqi, K.S. et al., "Group IV metal complexes of the dithiocarbamate ligand derived from propanediamine," Synthesis and Reactivity in Inorganic and Metal-Organic chemistry, 23:5, 685-693 Sep. 2006.

Karsch, H.H. et al., "'Hypervalent' molecules—low valency candidates for materials?," Organosilicon Chemistry VI: From Molecules to Materials, N. Auner and J. Weis, eds., 2005, Wiley-VCH Verlag GmbH, Weinheim, 194-284.

Negrebetsky, V.V. et al., "Dynamic stereochemistry of hypervalent silicon, germanium and tin compounds containing amidomethyl C,O-chelating ligands," Russian Chemical Bulleting, vol. 46, No. 11, Nov. 1997, 1807-1831.

Xu, C. et al., "Synthesis and characterization of neutral *cis*-hexacoordinate bis(β-diketonate) silicon(IV) complexes," Inorganic Chemistry 2004, 43, 1568-1573.

Beckmann, J. et al., "The origin of ring strain and conformational flexibility in tri- and tetrasiloxane rings and their heavier Group 14 congeners," Organosilicon Chemistry VI: From Molecules to Materials, N. Auner and J. Weis, eds., 2005, Wiley-VCH Verlag GmbH, Weinheim, 252-258.

Dona, N. et al., "Novel dimeric pentacoordinate silicon complexes: unusual reactivity of electron-rich aminosilane intermediates," Organosilicon Chemistry VI: From Molecules to Materials, N. Auner and J. Weis, eds., 2005, Wiley-VCH Verlag GmbH, Weinheim, 271-278.

Dransfeld, A. et al., "The effect of silyl anion substituents on the stability and NMR characteristics of cyclic polyphosphines—an ab initio-NMR Study," Organosilicon Chemistry VI: From Molecules to Materials, N. Auner and J. Weis, eds., 2005, Wiley-VCH Verlag GmbH, Weinheim, 240-244.

von Frantzius, G. et al., "Strong evidence for an unconventional 1,2-(C→P)-silyl migration: DFT structures and bond strengths (compliance constants)," Organosilicon Chemistry VI: From Molecules to Materials, N. Auner and J. Weis, eds., 2005, Wiley-VCH Verlag GmbH, Weinheim, 211-215.

Hassler, K. et al., "Preparations and x-ray structures of some silicon-phosphorus and silicon-arsenic cages," Organosilicon Chemistry VI: From Molecules to Materials, N. Auner and J. Weis, eds., 2005, Wiley-VCH Verlag GmbH, Weinheim, 228-232.

Herzog, U. et al., "Si NMR chemical shift tensors in organosilicon chalcogenides," Organosilicon Chemistry VI: From Molecules to Materials, N. Auner and J. Weis, eds., 2005, Wiley-VCH Verlag GmbH, Weinheim, 259-264.

Ionescu, E. et al., "Strong evidence for an unconventional 1,2-(C→P)-silyl migration: formation and reactions of a P-silyl phosphaalkene complex," Organosilicon Chemistry VI: From Molecules to Materials, N. Auner and J. Weis, eds., 2005, Wiley-VCH Verlag GmbH, Weinheim, 202-208.

Kliem, S. et al., "Silyl group migrations between oxygen and nitrogen in aminosiloxanes," Organosilicon Chemistry VI: From Molecules to Materials, N. Auner and J. Weis, eds., 2005, Wiley-VCH Verlag GmbH, Weinheim, 216-221.

Lange, H. et al., "Hypersilyltelluro-substituted silanes and $(Ph_2SiTe)_3$," Organosilicon Chemistry VI: From Molecules to Materials, N. Auner and J. Weis, eds., 2005, Wiley-VCH Verlag GmbH, Weinheim, 265-270.

Mehring, M. et al., "Homo- and heterometallic bismuth silanolates," Organosilicon Chemistry VI: From Molecules to Materials, N. Auner and J. Weis, eds., 2005, Wiley-VCH Verlag GmbH, Weinheim, 233-239.

Pietschnig, R. et al., "Terphenyl phosphanosilanes," Organosilicon Chemistry VI: From Molecules to Materials, N. Auner and J. Weis, eds., 2005, Wiley-VCH Verlag GmbH, Weinheim, 222-227.

Veith, M. et al., "Silanols as precursors to cyclo- and polysiloxanes," Organosilicon Chemistry VI: From Molecules to Materials, N. Auner and J. Weis, eds., 2005, Wiley-VCH Verlag GmbH, Weinheim, 245-251.

Wagler, J. et al., "Unique switching of coordination number with imine and enamine complexes of Group 14 elements," Organosilicon Chemistry VI: From Molecules to Materials, N. Auner and J. Weis, eds , 2005, Wiley-VCH Verlag GmbH, Weinheim, 279-284.

(56) References Cited

OTHER PUBLICATIONS

Ebsworth, E.A.V. et al., "The preparation and properties of some silyl esters," J. Chem. Soc. (A), 1967, pp. 69-72.

Gonzalez-Garcia et al., "Pentacoordinate mono(β-diketonato)- and hexacoordinate bis-(β-diketonato)-silicon(IV) complexes obtained from (thiocyanato-N)hydridosilanes," Polyhedron 41 (2012), pp. 127-133.

Junold, K. et al., "Bis[N,N'-diisopropylbenzamidinato(−)]silicon(II): a silicon(II) compound with both a bidentate and a monodentate amidinato ligand," Angew. Chem. Int. Ed. 2012, 51, pp. 7020-7023.

Junold, K. et al., "Novel neutral hexacoordinate benzamidinatosilicon(IV) complexes with $SiN_3OF_2$, $SiN_3OCl_2$, $SiN_3OBr_2$, $SiN_5O$ and $SiN_3O_3$ skeletons," Dalton Trans., 2011, 40, pp. 9844-9857.

Karsch, H.H. et al., "Bis(amidinate) complexes of silicon and germanium," Eur. J. Inorg. Chem. 1998, pp. 433-436.

Karsch, H.H. et al., "Silicon and germanium amidinates" in Organosilicon Chemistry Set: From Molecules to Materials (eds N. Auner and J. Weis), Wiley-VCH Verlag GmbH, Weinheim, Germany, pp. 287-293, 2000.

Karsch, H.H. et al., "Silicon and germanium compounds with amidinate ligands," Organosilicon Chemistry V: From Molecules to Materialsk, Norbert Auner and Johann Weis, eds., 2003, Wiley-VCH, pp. 270-276.

International Search Report for corresponding PCT/US2013/051244, Oct. 16, 2013.

International Search Report for related PCT/US2013/051249, Oct. 16, 2013.

International Search Report for related PCT/US2013/051255, Oct. 16, 2013.

International Search Report for related PCT/US2013/051264, Oct. 16, 2013.

* cited by examiner

US 9,371,338 B2

ORGANOSILANE PRECURSORS FOR ALD/CVD SILICON-CONTAINING FILM APPLICATIONS

CROSS-REFERENCE TO RELATED APPLICATIONS

This application is a 371 of International PCT Application No. PCT/US2013/051244 filed Jul. 19, 2013 which claims priority to U.S. provisional application No. 61/674,103, filed Jul. 20, 2012, the entire contents of each being incorporated herein by reference.

TECHNICAL FIELD

Disclosed are Si-containing thin film forming precursors, methods of synthesizing the same, and methods of using the same to deposit silicon-containing films using vapor deposition processes for manufacturing semiconductors, photovoltaics, LCD-TFT, flat panel-type devices, refractory materials, or aeronautics.

BACKGROUND

Si-containing thin films are used widely in the semiconductor, photovoltaic, LCD-TFT, flat panel-type device, refractory material, or aeronautic industries. Si-containing thin films may be used, for example, as dielectric materials having electrical properties which may be insulating ($SiO_2$, SiN, SiCN, SiCOH, $MSiO_x$, wherein M is Hf, Zr, Ti, Nb, Ta, or Ge and x is greater than zero), Si-containing thin films may be used as conducting films, such as metal silicides or metal silicon nitrides. Due to the strict requirements imposed by downscaling of electrical device architectures towards the nanoscale (especially below 28 nm node), increasingly fine-tuned molecular precursors are required which meet the requirements of volatility (for ALD process), lower process temperatures, reactivity with various oxidants and low film contamination, in addition to high deposition rates, conformality and consistency of films produced.

It is well known that silane ($SiH_4$) can be used for thermal CVD. However this molecule is pyrophoric which makes this room temperature gas a challenge to handle safely. CVD methods employing halosilanes (such as dichlorosilane $SiH_2Cl_2$) have been used. However, these may require long purge times, cause halogen contamination of the films and particle formation (from ammonium chloride salts), and even damage certain substrates resulting in undesirable interfacial layer formation. Partially replacing halogen with alkyl groups may yield some improvement, but at a cost of detrimental carbon contamination within the film.

Organoaminosilanes have been used as precursors for CVD of Si-containing films. U.S. Pat. No. 7,192,626 to Dussarrat et al. reports the use of trisilylamine $N(SiH_3)_3$ for deposition of SiN films. Other reported precursors include diisopropylaminosilane [$SiH_3(NiPr_2)$] and analogous $SiH_3(NR_2)$ compounds (see, e.g., U.S. Pat. No. 7,875,312 to Thridandam et al.) and phenylmethylaminosilane [$SiH_3(NPhMe)$] and related substituted silylanilines (see, e.g., EP 2392691 to Xiao et al.).

Another related class of Si precursors for CVD of Si-containing films is given by the general formula $(R^1R^2N)_xSiH_{4-x}$ wherein x is between 1 and 4 and the R substituents are independently H, C1-C6 linear, branched, or cyclic carbon chains (see, e.g., WO2006/097525 to Dussarrat et al.).

Hunks et al. disclose a wide range of Si-containing precursors in US2010/0164057, including silicon compounds having the formula $R_{4-x}SiL_x$, wherein x is an integer having a value from 1 to 3; R may be selected from H, branched and unbranched C1-C6 alkyl, C3-C8 cycloalkyl, and C6-C13 aryl groups; and L may be selected from isocyanato, methylethylketoxime, trifluoroacetate, triflate, acyloxy, β-diketiminate, β-di-iminate, amidinate, guanidinate, alkylamino, hydride, alkoxide, or formate ligands. Pinnavaia et al. claim a method for the preparation of a porous synthetic, semi-crystalline hybrid organic-inorganic silicon oxide composition from silicon acetylacetonate and silicon 1,3-diketonate precursors (U.S. Pat. No. 6,465,387).

Despite the wide range of choices available for the deposition of Si containing films, additional precursors are continuously sought to provide device engineers the ability to tune manufacturing process requirements and achieve films with desirable electrical and physical properties.

Notation and Nomenclature

Certain abbreviations, symbols, and terms are used throughout the following description and claims, and include:

As used herein, the indefinite article "a" or "an" means one or more.

As used herein, the term "independently" when used in the context of describing R groups should be understood to denote that the subject R group is not only independently selected relative to other R groups bearing the same or different subscripts or superscripts, but is also independently selected relative to any additional species of that same R group. For example in the formula $MR^1_x(NR^2R^3)_{(4-x)}$, where x is 2 or 3, the two or three $R^1$ groups may, but need not be identical to each other or to $R^2$ or to $R^3$. Further, it should be understood that unless specifically stated otherwise, values of R groups are independent of each other when used in different formulas.

As used herein, the term "alkyl group" refers to saturated functional groups containing exclusively carbon and hydrogen atoms. Further, the term "alkyl group" refers to linear, branched, or cyclic alkyl groups. Examples of linear alkyl groups include without limitation, methyl groups, ethyl groups, propyl groups, butyl groups, etc. Examples of branched alkyls groups include without limitation, t-butyl. Examples of cyclic alkyl groups include without limitation, cyclopropyl groups, cyclopentyl groups, cyclohexyl groups, etc.

As used herein, the term "aryl" refers to aromatic ring compounds where one hydrogen atom has been removed from the ring. As used herein, the term "heterocycle" refers to a cyclic compound that has atoms of at least two different elements as members of its ring.

As used herein, the abbreviation "Me" refers to a methyl group; the abbreviation "Et" refers to an ethyl group; the abbreviation "Pr" refers to any propyl group (i.e., n-propyl or isopropyl); the abbreviation "iPr" refers to an isopropyl group; the abbreviation "Bu" refers to any butyl group (n-butyl, iso-butyl, t-butyl, sec-butyl); the abbreviation "tBu" refers to a tert-butyl group; the abbreviation "sBu" refers to a sec-butyl group; the abbreviation "iBu" refers to an iso-butyl group; the abbreviation "Ph" refers to a phenyl group; the abbreviation "Am" refers to any amyl group (iso-amyl, sec-amyl, tert-amyl); the abbreviation "Cy" refers to a cyclic alkyl group (cyclobutyl, cyclopentyl, cyclohexyl, etc.); and the abbreviation "R-amd" refers to an R—N—C(Me)-N—R amidinate ligand, with R being an alkyl group (e.g., iPr-amd is iPr—N—C(Me)-N-iPr).

As used herein, the acronym "SRO" stands for a Strontium Ruthenium Oxide film; the acronym "HCDS" stands for hexachlorodisilane; and the acronym "PODS" stands for pentachlorodisilane.

The standard abbreviations of the elements from the periodic table of elements are used herein. It should be understood that elements may be referred to by these abbreviations (e.g., Si refers to silicon, N refers to nitrogen, O refers to oxygen, C refers to carbon, etc.).

BRIEF DESCRIPTION OF THE DRAWINGS

For a further understanding of the nature and objects of the present invention, reference should be made to the following detailed description, taken in conjunction with the accompanying drawings, in which like elements are given the same or analogous reference numbers and wherein.

SUMMARY

Figure 1:
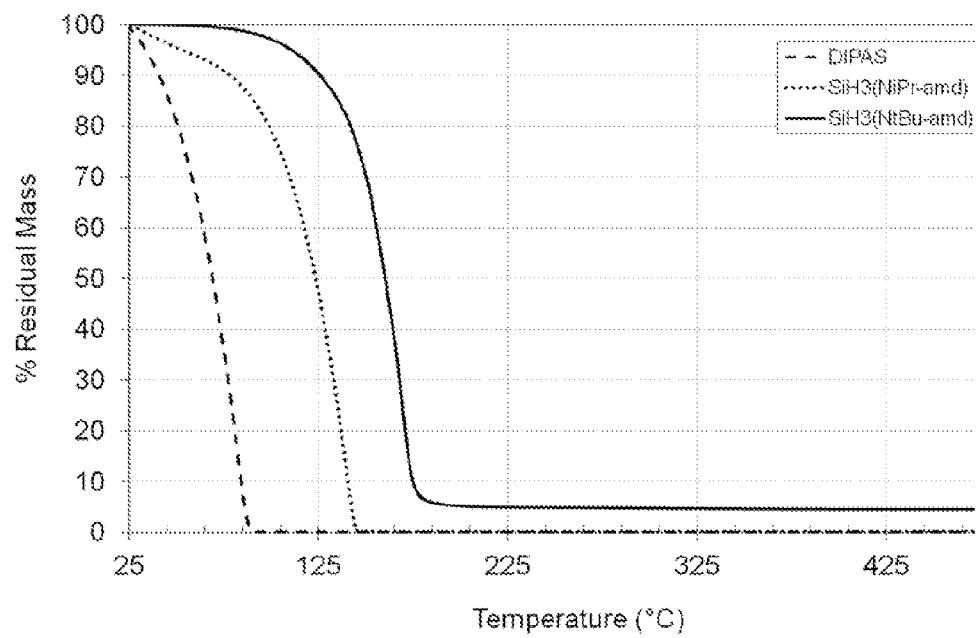
FIG. 1 is thermogravimetric analysis (TGA) graph demonstrating the percentage of weight loss with temperature change for $SiH_3(N^iPr\text{-amd})$ and $SiH_3$ ($N^{tBu}$-amd) as compared to that of DiPAS (diisopropylaminosilane)

Disclosed are organosilane molecules having the following formula:

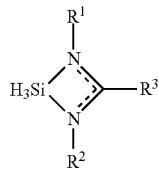

wherein $R^1$ and $R^2$ may each independently be H, a C1 to C6 alkyl group, or a C3-C20 aryl or heterocycle group and $R^3$ may be H, a C1 to C6 alkyl group, a C3-C20 aryl or heterocycle group, an amino group, an alkoxy group, or a halogen;

$R^1$ and $R^2$ and/or $R^2$ and $R^3$ being joined to form cyclic chains;

the organosilane molecule having the following formula:

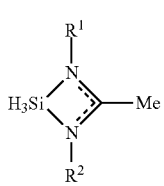

wherein $R^1$ and $R^2$ may each independently be a C1 to C6 alkyl group;

the organosilane molecule being $H_3Si(N^iPr\text{-amd})$;
the organosilane molecule having the following formula:

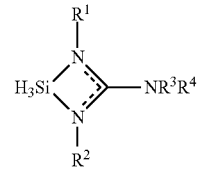

wherein $R^1$, $R^2$, $R^3$ and $R^4$ may each independently be H, a C1 to C6 alkyl group, or a C3-C20 aryl or heterocycle;
the organosilane molecule being $H_3Si(\text{—}(^iPr)N\text{—}C(NMe_2)\text{-}N(^iPr)\text{—})$;
the organosilane molecule having the following formula:

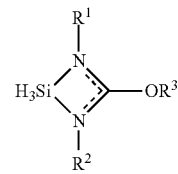

wherein $R^1$, $R^2$, and $R^3$ may each independently be H, a C1 to C6 alkyl group, or a C3-C20 aryl or heterocycle;
the organosilane molecule being $H_3Si(\text{-}(iPr)N\text{—}C(OMe)\text{-}N(iPr)\text{—})$;
the organosilane molecule having the following formula:

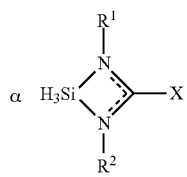

wherein $R^1$ and $R^2$ may each independently be H, a C1 to C6 alkyl group, or a C3-C20 aryl or heterocycle and X may be Cl, Br, I, or F; and
the organosilane molecule being $H_3Si(\text{-}(iPr)N\text{—}C(Cl)\text{—}N(iPr)\text{—})$.

Also disclosed are Si-containing thin film forming precursors having the following formula:

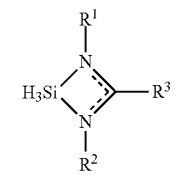

wherein $R^1$ and $R^2$ may each independently be H, a C1 to C6 alkyl group, or a C3-C20 aryl or heterocycle group and $R^3$ may be H, a C1 to C6 alkyl group, a C3-C20 aryl or heterocycle group, an amino group, an alkoxy group, or a halogen;
$R^1$ and $R^2$ and/or $R^2$ and $R^3$ being joined to form cyclic chains;
the Si-containing thin film forming precursor having the following formula:

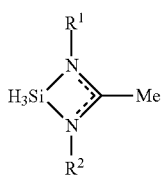

wherein R¹ and R² may each independently be a C1 to C6 alkyl group;
the Si-containing thin film forming precursor being H₃Si (N'Pr-amd);
the Si-containing thin film forming precursor having the following formula:

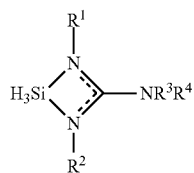

wherein R¹, R², R³ and R⁴ may each independently be H, a C1 to C6 alkyl group, or a C3-C20 aryl or heterocycle;
the Si-containing thin film forming precursor being H₃Si (—(ⁱPr)N—C(NMe₂)-N(ⁱPr)—);
the Si-containing thin film forming precursor having the following formula:

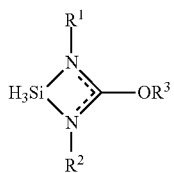

wherein R¹, R², and R³ may each independently be H, a C1 to C6 alkyl group, or a C3-C20 aryl or heterocycle; and
the Si-containing thin film forming precursor being H₃Si (-(iPr)N—C(OMe)-N(iPr)—);
the Si-containing thin film forming precursor having the following formula:

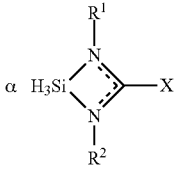

wherein R¹ and R² may each independently be H, a C1 to C6 alkyl group, or a C3-C20 aryl or heterocycle and X may be Cl, Br, I, or F; and
the Si-containing thin film forming precursor being H₃Si (-(iPr)N—C(Cl)—N(iPr)—).

Also disclosed are methods of depositing a Si-containing layer on a substrate.

At least one organosilane precursor disclosed above is introduced into a reactor having at least one substrate disposed therein. At least part of the organosilane precursor is deposited onto the at least one substrate to form a Si-containing layer using a vapor deposition method. The disclosed methods may have one or more of the following aspects:

- introducing into the reactor a vapor comprising at least one second precursor;
- an element of the at least one second precursor being selected from the group consisting of group 2, group 13, group 14, transition metal, lanthanides, and combinations thereof;
- the element of the at least one second precursor being selected from Mg, Ca, Sr, Ba, Zr, Hf, Ti, Nb, Ta, Al, Si, Ge, Y, or lanthanides;
- introducing into the reactor at least one co-reactant;
- the co-reactant being selected from the group consisting of O₂, O₃, H₂O, H₂O₂, NO, NO₂, a carboxylic acid, radicals thereof, and combinations thereof;
- the co-reactant being plasma treated oxygen;
- the co-reactant being ozone;
- the Si-containing layer being a silicon oxide layer;
- the co-reactant being selected from the group consisting of H₂, NH₃, (SiH₃)₃N, hydridosilanes (such as SiH₄, Si₂H₆, Si₃H₈, Si₄H₁₀, Si₆H₁₀, Si₆H₁₂), chlorosilanes and chloropolysilanes (such as SiHCl₃, SiH₂Cl₂, SiH₃Cl, Si₂Cl₆, Si₂HCl₅, Si₃Cl₈), alkysilanes (such as Me₂SiH₂, Et₂SiH₂, MeSiH₃, EtSiH₃), hydrazines (such as N₂H₄, MeHNNH₂, MeHNNHMe), organic amines (such as NMeH₂, NEtH₂, NMe₂H, NEt₂H, NMe₃, NEt₃, (SiMe₃)₂NH), pyrazoline, pyridine, B-containing molecules (such as B₂H₆, 9-borabicylo[3,3,1]none, trimethylboron, triethylboron, borazine), alkyl metals (such as trimethylaluminum, triethylaluminum, dimethylzinc, diethylzinc), radical species thereof, and mixtures thereof.
- the co-reactant being selected from the group consisting of H₂, NH₃, SiH₄, Si₂H₆, Si₃H₈, SiH₂Me₂, SiH₂Et₂, N(SiH₃)₃, hydrogen radicals thereof, and mixtures thereof;
- the co-reactant being plasma-treated;
- the co-reactant being remote plasma-treated;
- the co-reactant not being plasma-treated;
- the co-reactant being H₂;
- the co-reactant being NH₃;
- the co-reactant being HCDS;
- the co-reactant being PODS;
- the co-reactant being tetrachlorosilane;
- the co-reactant being trichlorosilane;
- the co-reactant being hexachlorocyclohexasilane;
- the vapor deposition process being a chemical vapor deposition process;
- the vapor deposition process being an atomic layer deposition (ALD) process;
- the vapor deposition process being a spatial ALD process;
- the silicon-containing layer being Si;
- the silicon-containing layer being SiO₂;
- the silicon-containing layer being SiN;
- the silicon-containing layer being SiON;
- the silicon-containing layer being SiCN; and
- the silicon-containing layer being SiCOH.

DESCRIPTION OF PREFERRED EMBODIMENTS

Disclosed are Si-containing thin film forming precursors, methods of synthesizing the same, and methods of using the same to deposit silicon-containing films using vapor deposition processes for manufacturing semiconductors, photovoltaics, LCD-TFT, flat panel-type devices, refractory materials, or aeronautics.

The disclosed organosilane precursors have the following formula:

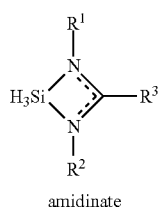

amidinate wherein $R^1$ and $R^2$ may each independently be H, a C1 to C6 alkyl group, or a C3-C20 aryl or heterocycle group and $R^3$ may be H, a C1 to C6 alkyl group, a C3-C20 aryl or heterocycle group, an amino group, an alkoxy group, or a halogen. $R^1$ and $R^2$ and/or $R^2$ and $R^3$ may be joined to form cyclic chains.

As illustrated in the formula, the nitrogen atoms are bonded to the silicon atom, resulting in a pentacoordinate Si(IV) center. The carbon atom in the backbone of the bidentate monoanionic ligand is sp$^2$ hybridized, resulting in a delocalized charge across the ligand. Each of the nitrogen and carbon atoms may independently be substituted by H, C1-C6 alkyl groups, aryl groups, or heterocycle groups.

The disclosed organosilane precursors may be more reactive than other $R_{4-x}SiL_x$ precursors due to hypercoordination at the silicon atom. In other words, although the silicon atom is +IV, the three hydrogen bonds and the monoanionic chelating ligand results in a total of 5 bonds to the silicon atom.

One of ordinary skill in the art will recognize that the use of hydrogen or alkyl, aryl or heterocycle groups having less carbon atoms (i.e., H, C1 or C2) in any of the R groups will produce a molecule having higher volatility as compared to a molecule having alkyl, aryl or heterocycle groups with more carbons (i.e., C4+). Due to their increased nitrogen content from the two nitrogen atoms on the —N—C—N— ligand, these molecules may be used to produce silicon-containing films that also contain nitrogen, such as SiN, SiCN, SiON, MSiN, or MSiON, wherein M is an element such as Hf, Zr, Ti, Nb, Ta, or Ge, or to tune the amount of nitrogen in those films.

When $R^3$ is Me, the resulting precursor is an amidinate containing compound having the following formula:

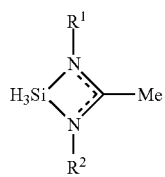

wherein $R^1$ and $R^2$ may each independently be H, a C1 to C6 alkyl group, or a C3-C20 aryl or heterocycle group. Preferably, R1 and R2 are each independently a C1 to C6 alkyl group.

The amidinate precursors may be synthesized by combining a hydrocarbon solution of SiXH$_3$, wherein X is Cl, Br, I, or triflate (SO$_3$CF$_3$), with a neat or hydrocarbon solution of the ligand compound, such as Li[R$^1$NC(R$^2$)NR$^3$] (or Li(amd)), under atmosphere of nitrogen, the outlet of the mixing flask being connected to an oil bubbler to inhibit backflow of air and moisture.

A second synthetic route to the disclosed amidinate precursors is by reaction of the protonated ligand (R$^1$N=C(R$^2$)—NRH$^3$) with either a neat or a hydrocarbon solution of a dialkylaminosilane [SiH$_3$(NR$_2$)] performed under an inert atmosphere.

Alternatively, the disclosed amidinate precursors may be synthesized by reaction of SiH$_n$Cl$_{4-n}$ with a single equivalent of the ligand compound (i.e., Li[R$^1$NC(R$^2$)NR$^3$] or Li(amd)) and subsequent reduction using a selected metal hydride, such as LAH (lithium aluminum hydride).

In all three synthesis routes, the resulting solution may be stirred at room temperature overnight. Exemplary hydrocarbon solutions suitable for these synthesis methods include diethyl ether, pentane, hexane, or toluene. The resulting suspension is filtered and the resulting solution distilled to remove solvent. Purification of the resulting liquid or solid is carried out by distillation or sublimation, respectively. Except for the ligand compounds Li(amd), all of the starting materials are commercially available. The ligand compound may be synthesized by combining a hydrocarbon solution of metalorganic salt (i.e., alkyl lithium) to a hydrocarbon solution of the appropriate carbodiimide (i.e., R$^1$N=C=NR$^3$). Additional synthesis details are provided in the Examples.

Exemplary amidinate precursors include:

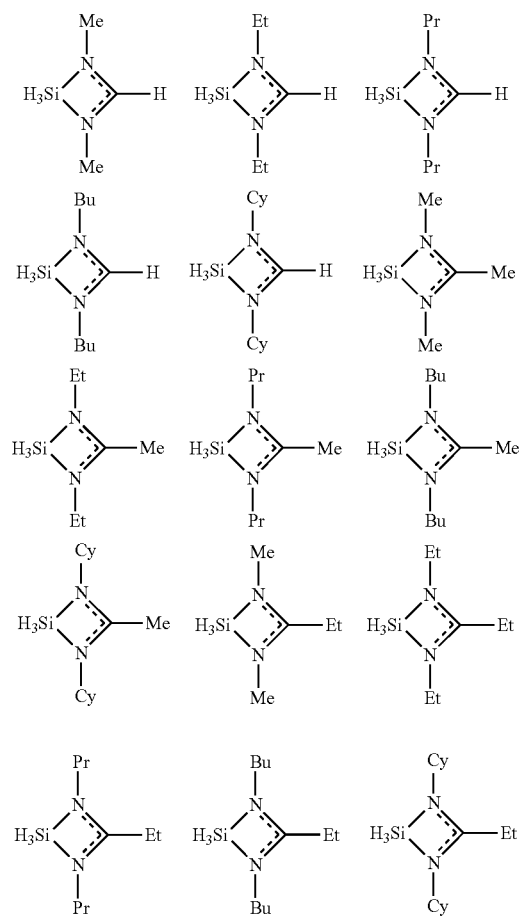

-continued
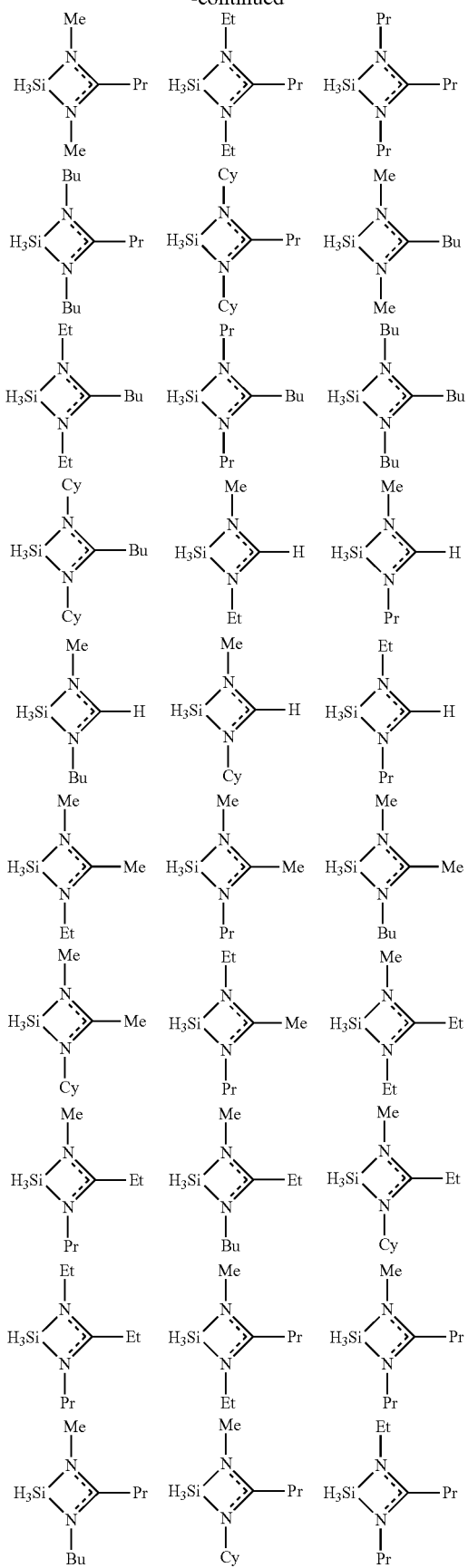
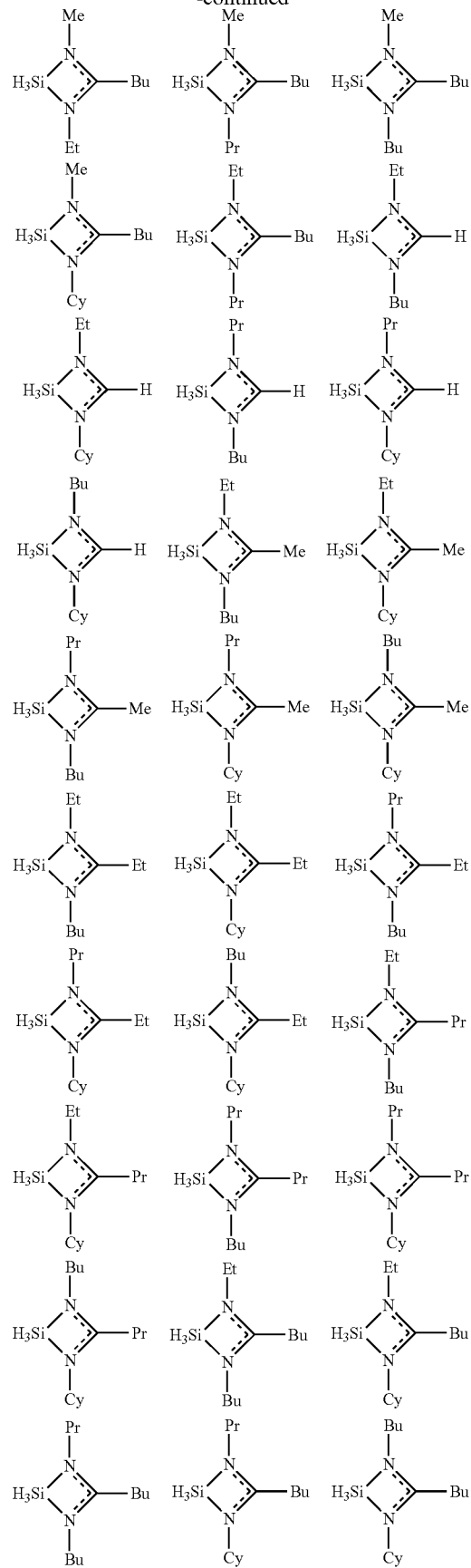

-continued

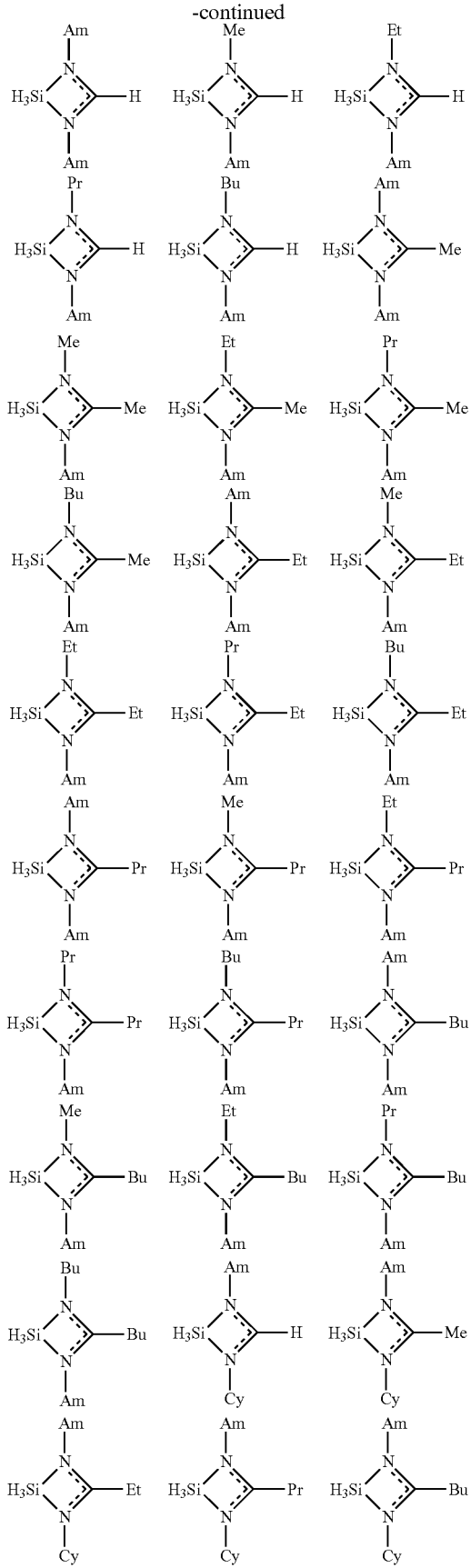

Preferably, the amidinate precursor is SiH$_3$(N$^i$Pr-amd).

When R$^3$ is amino group (i.e., NR$^3$R$^4$), the resulting precursor is a guanidinate containing compound having the following formula:

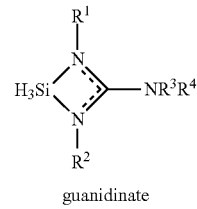

guanidinate wherein R$^1$, R$^2$, R$^3$, and R$^4$ may each independently be H, a C1 to C6 alkyl group, C3-C20 aryl, or heterocycle. Due to their increased nitrogen content when compared to the other molecules, these molecules may be used to produce silicon-containing films that also contain nitrogen, such as SiN or SiON, or to tune the amount of nitrogen in a SiN or SiON containing film.

The guanidinate precursors may be synthesized by combining a hydrocarbon solution of SiXH$_3$, wherein X is Cl, Br, I, or triflate (SO$_3$CF$_3$), with a neat or hydrocarbon solution of the ligand compound, such as Li[R$^1$NC(NR$^3$R$^4$)NR$^2$] (or Li(gnd)), under atmosphere of nitrogen, the outlet of the mixing flask being connected to an oil bubbler to inhibit backflow of air and moisture.

A second synthetic route to the disclosed guanidinate precursors is by reaction of the protonated ligand (R$^1$N═C(NR$^3$R$^4$)—NR$^2$H) with either a neat or a hydrocarbon solution of a dialkylaminosilane [SiH$_3$(NR$_2$)] performed under an inert atmosphere.

Alternatively, the disclosed guanidinate precursors may be synthesized by reaction of SiH$_n$Cl$_{4-n}$ with a single equivalent of the ligand compound (i.e., Li[R$^1$NC(NR$^3$R$^4$)NR$^2$] or Li(gnd)) and subsequent reduction using a selected metal hydride, such as LAH (lithium aluminum hydride).

In all three synthesis routes, the resulting solution may be stirred at room temperature overnight. Exemplary hydrocarbon solutions suitable for these synthesis methods include diethyl ether, pentane, hexane, or toluene. The resulting suspension is filtered and the resulting solution distilled to remove solvent. Purification of the resulting liquid or solid is carried out by distillation or sublimation, respectively. Except for the ligand compounds Li(gnd), all of the starting materials are commercially available. The ligand compound may be synthesized by combining a hydrocarbon solution of metalorganic salt (i.e., lithium amide —Li(NR$^3$R$^4$)) to a hydrocarbon solution of the appropriate carbodiimide (i.e., R$^1$N═C═NR$^2$).

Exemplary guanidinate precursors include:

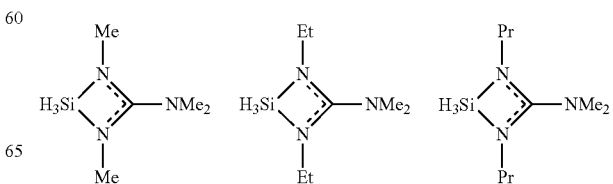

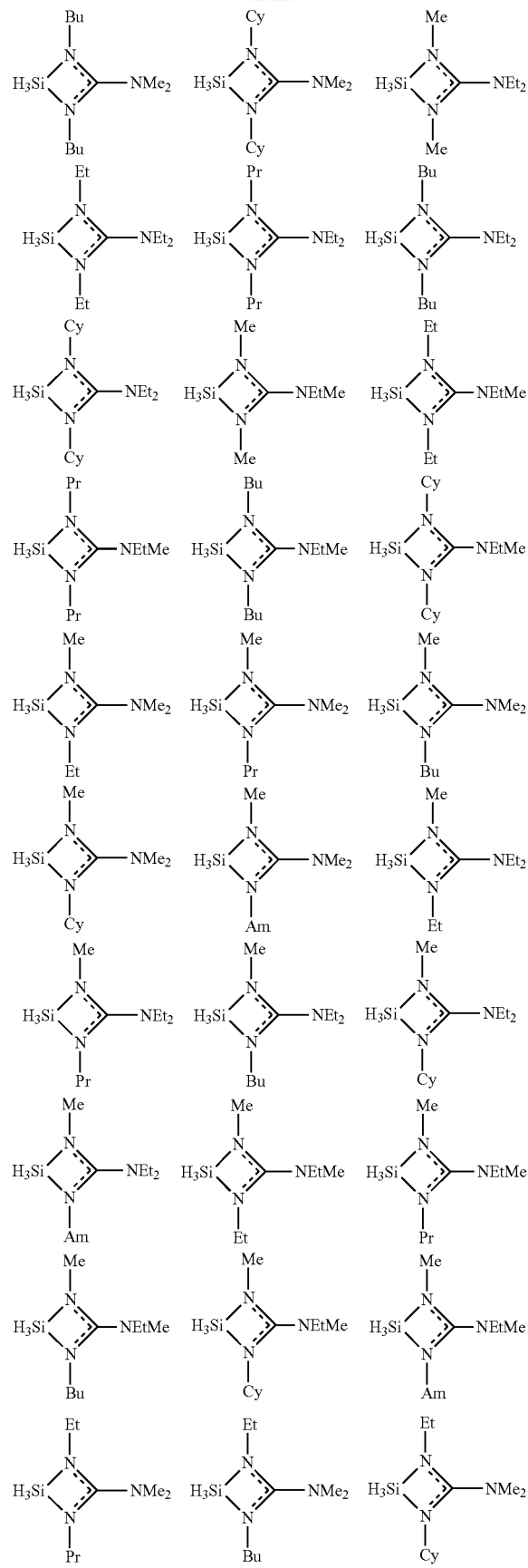
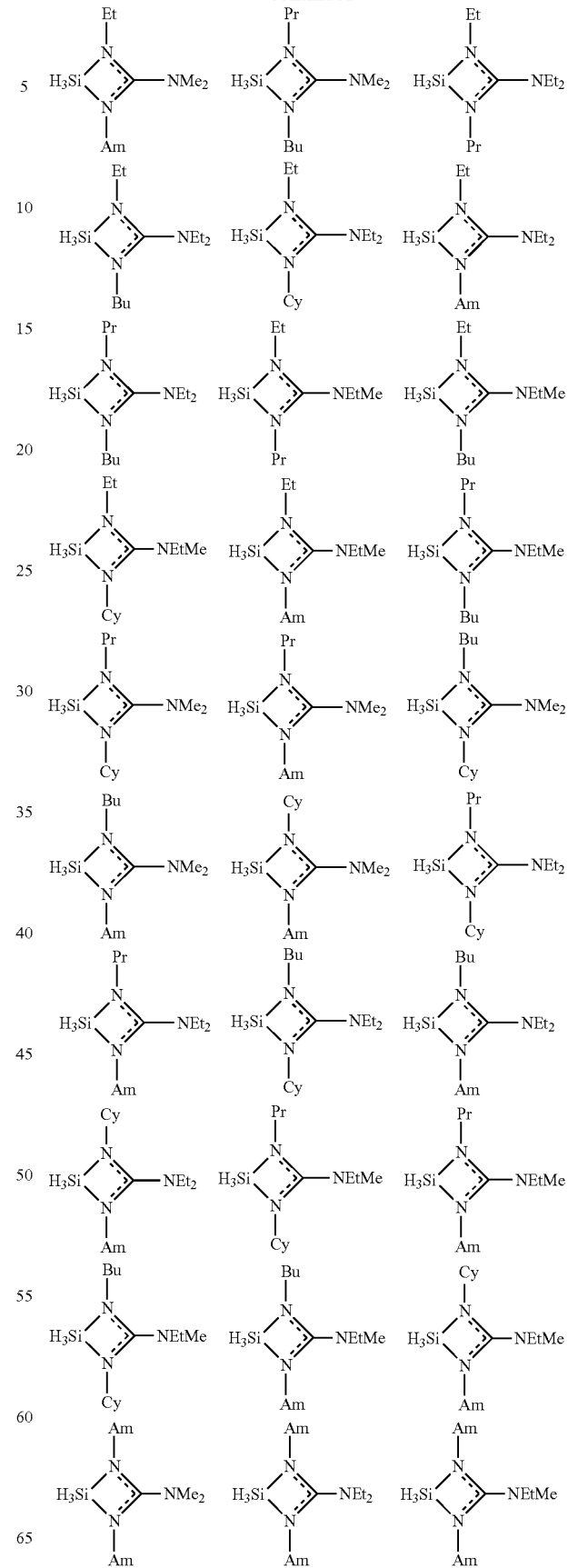

-continued
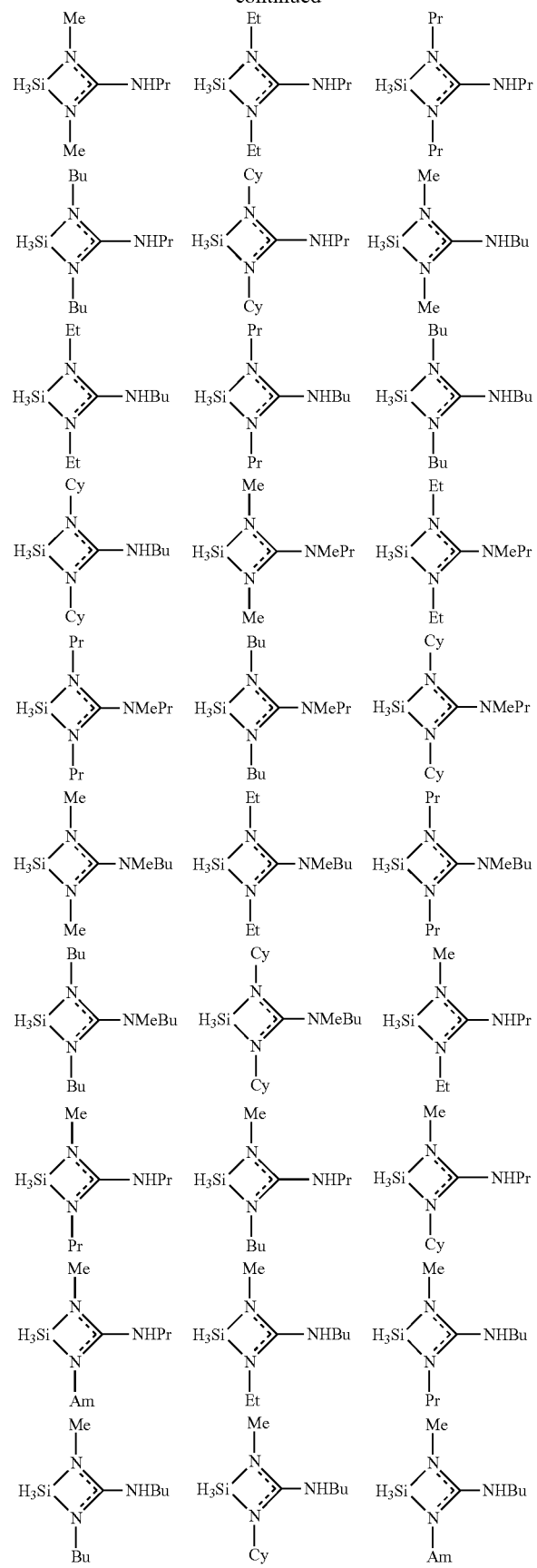
-continued
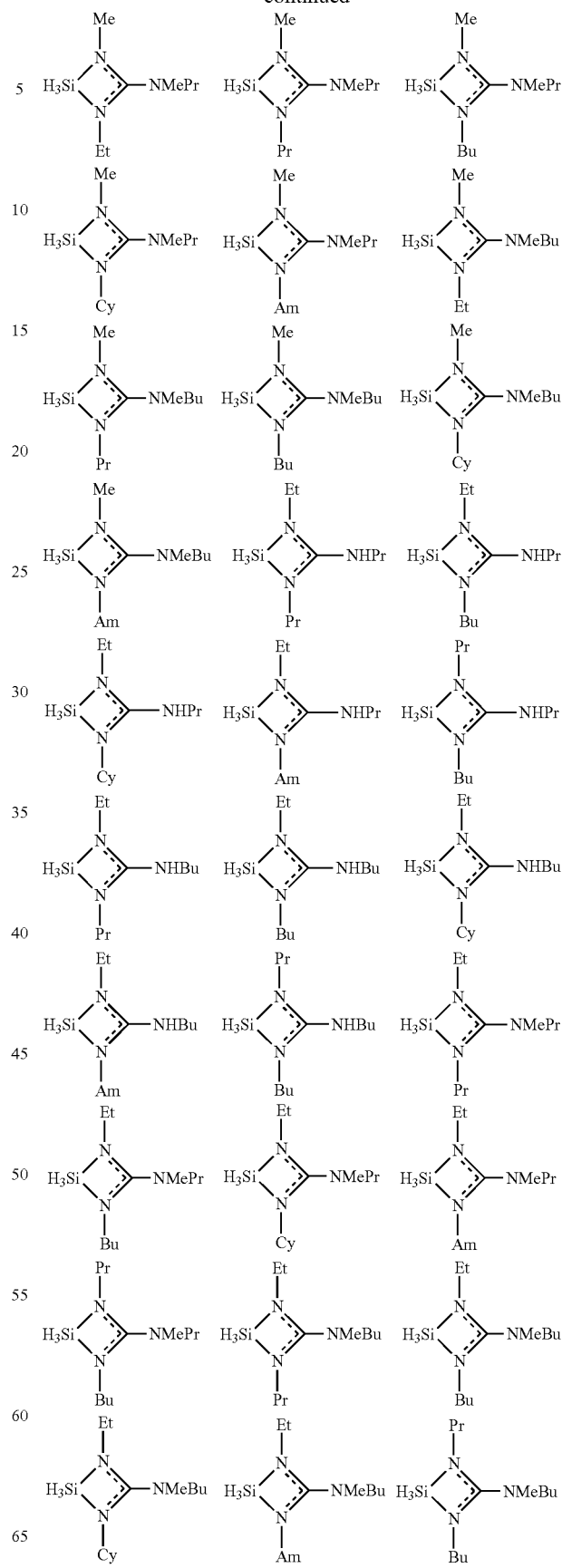

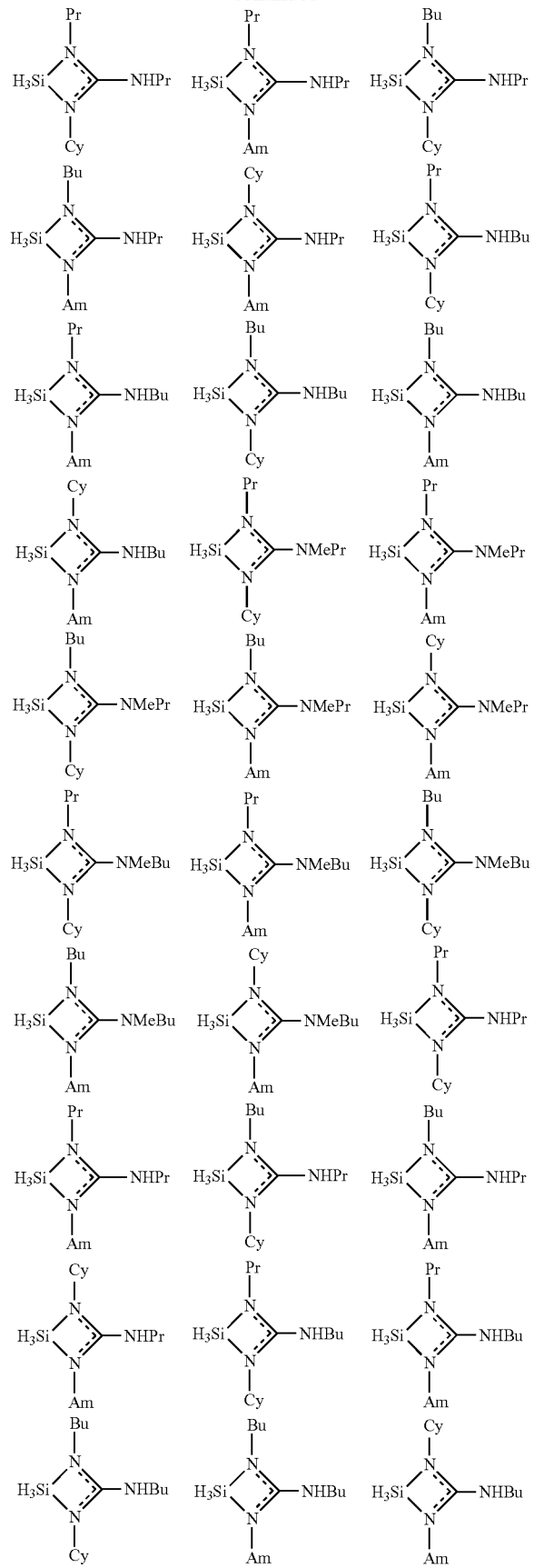

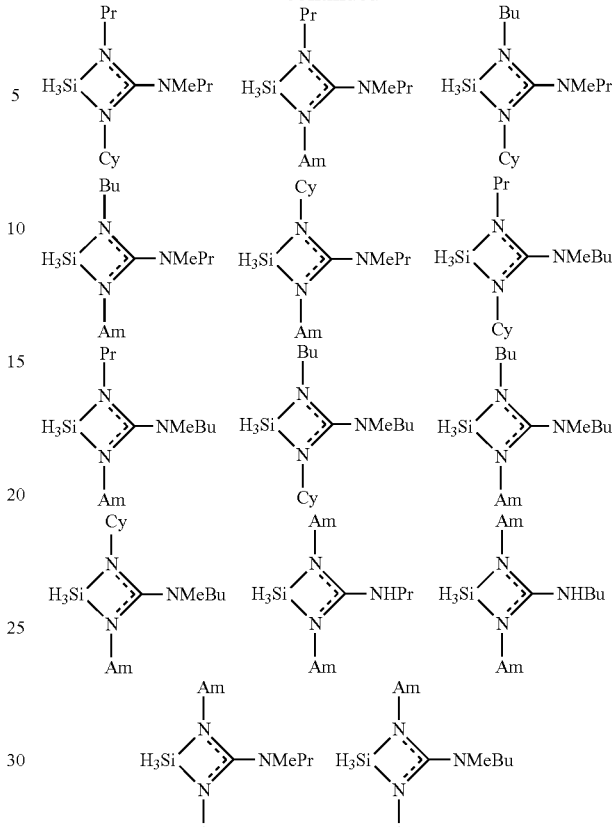

Preferably, the guanidinate precursor is H₃Si(—(ⁱPr)N—C(NMe₂)-N(ⁱPr)—).

When $R^3$ is an alkoxy group (i.e., $OR^3$), the resulting precursor is an isoureate containing compound having the following formula:

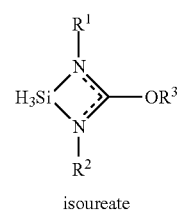

isoureate wherein $R^1$, $R^2$, and $R^3$ may each independently be H, a C1 to C6 alkyl group, or a C3-C20 aryl or heterocycle. Due to their increased oxygen content when compared to the other molecules, these molecules may be used to produce silicon-containing films that also contain oxygen, such as $SiO_2$ or SiON, or to tune the amount of oxygen in a $SiO_2$ or SiON containing film.

The isoureate precursors may be synthesized by combining a hydrocarbon solution of SiXH₃, wherein X is Cl, Br, I, or triflate (SO₃CF₃), with a neat or hydrocarbon solution of the ligand compound, such as Li[R¹NC(OR³)NR²] (or Li(iso)), under atmosphere of nitrogen, the outlet of the mixing flask being connected to an oil bubbler to inhibit backflow of air and moisture.

A second synthetic route to the disclosed isoureate precursors is by reaction of the protonated ligand (R¹N═C(OR³)—

NR²H) with either a neat or a hydrocarbon solution of a dialkylaminosilane [SiH₃(NR₂)] performed under an inert atmosphere.

Alternatively, the disclosed isoureate precursors may be synthesized by reaction of SiH$_n$Cl$_{4-n}$ with a single equivalent of the ligand compound (i.e., Li[R¹NC(OR³)NR²] or Li(iso)) and subsequent reduction using a selected metal hydride, such as LAH (lithium aluminum hydride).

In all three synthesis routes, the resulting solution may be stirred at room temperature overnight. Exemplary hydrocarbon solutions suitable for these synthesis methods include diethyl ether, pentane, hexane, or toluene. The resulting suspension is filtered and the resulting solution distilled to remove solvent. Purification of the resulting liquid or solid is carried out by distillation or sublimation, respectively. Except for the ligand compounds Li(iso), all of the starting materials are commercially available. The ligand compound may be synthesized by combining a hydrocarbon solution of metalorganic salt (i.e., lithium alkoxide —Li(OR³)) to a hydrocarbon solution of the appropriate carbodiimide (i.e., R¹N=C=NR²).

Exemplary isoureate precursors include:

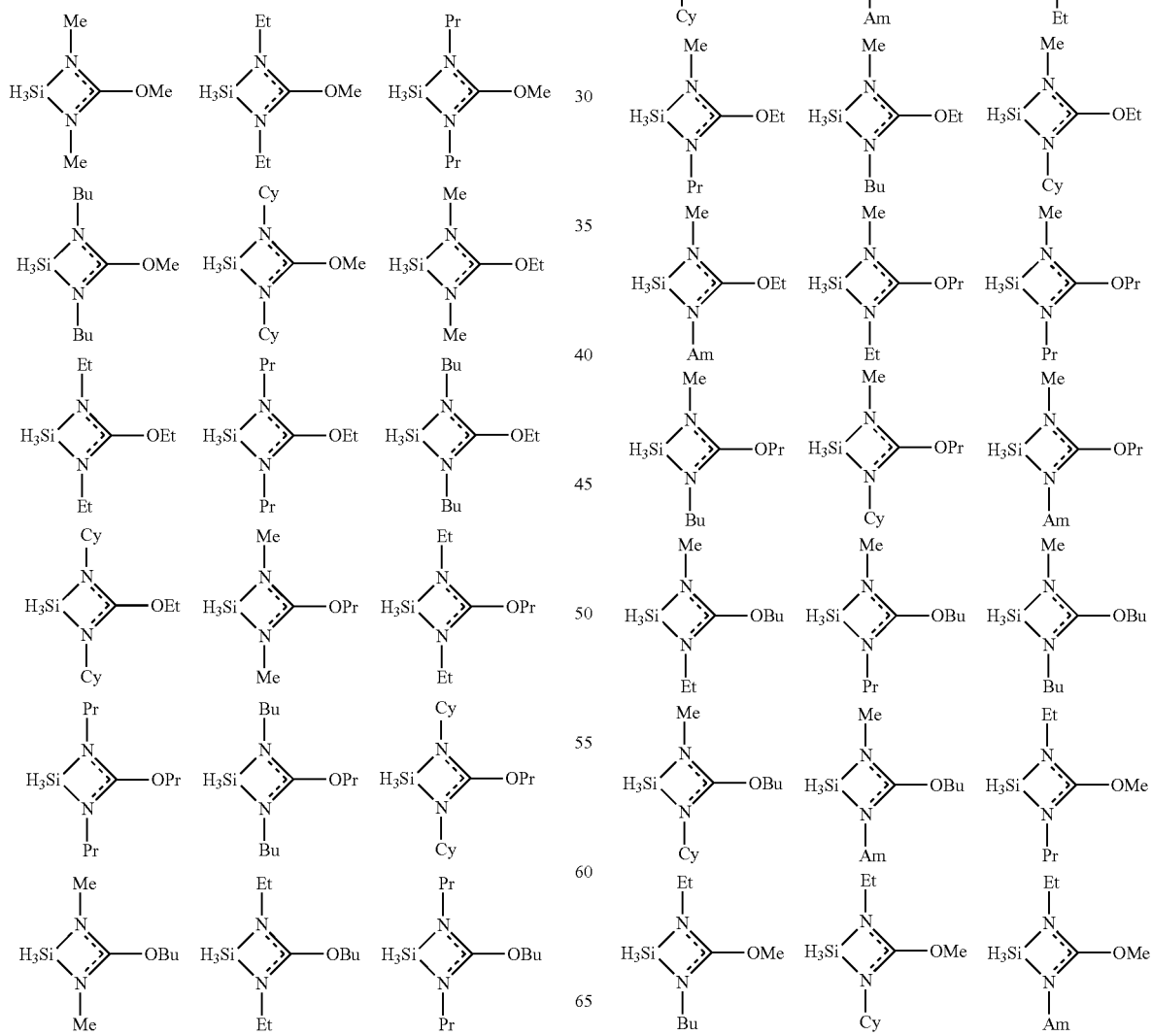

-continued

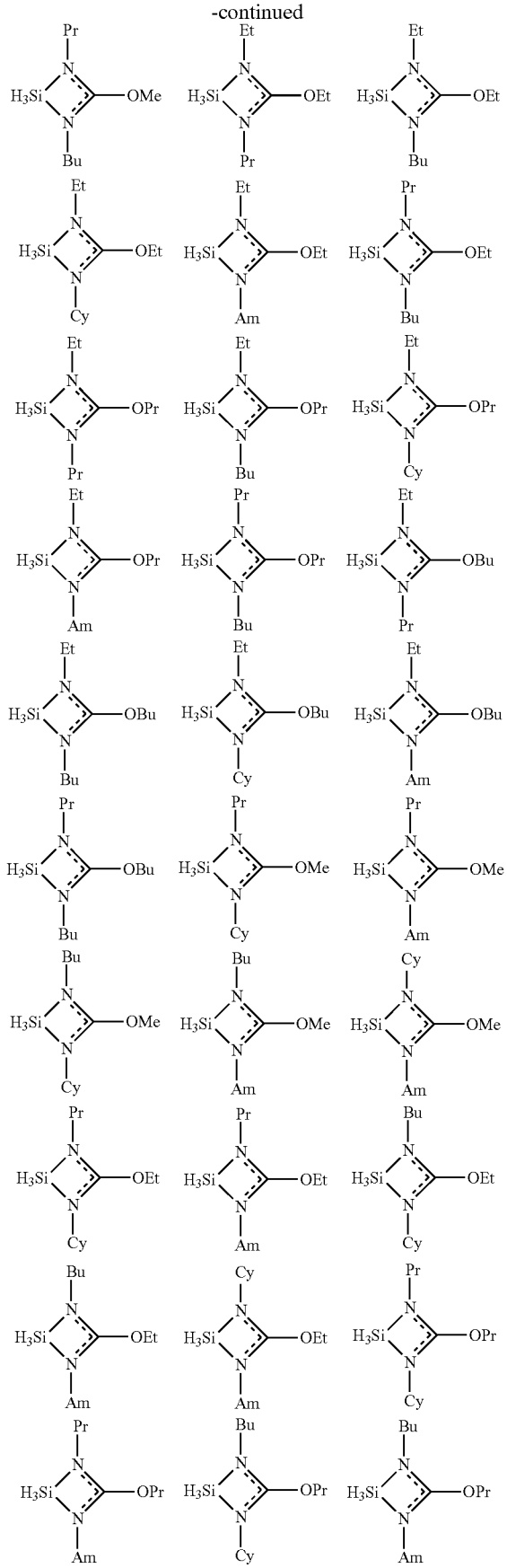

-continued

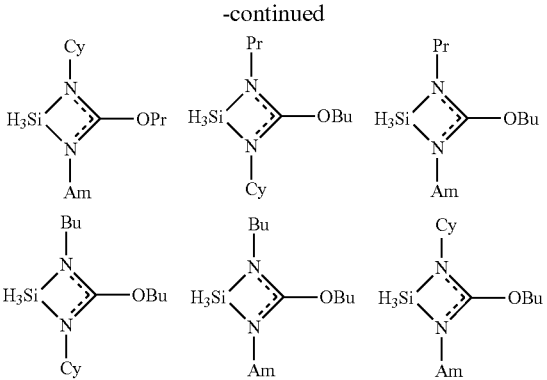

Preferably, the isoureate precursor is $H_3Si(-(iPr)N-C(OMe)-N(iPr)-)$.

When $R^3$ is a halogen (i.e., X), the resulting precursor is a α-haloamidinate containing compound having the following formula:

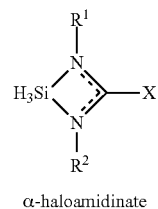

α-haloamidinate wherein $R^1$ and $R^2$ may each independently be H, a C1 to C6 alkyl group, or a C3-C20 aryl or heterocycle and X may be Cl, Br, I, or F. The halogen atom may improve conformality in atomic layer deposition of amorphous silicon.

The alpha-haloamidinate precursors may be synthesized by combining a hydrocarbon solution of a di-substituted urea derivative $R^1HN-(C=O)-NHR^2$ with a hydrocarbon solution of $O=CX_2$, as described by Neubauer et al. (Chemische Berichte, 1964, 97(5), 1232-1245). A hydrocarbon solution of one molar equivalent of an appropriate base (such as potassium hexamethyldisilazide) is added to the reaction mixture and the resulting suspension filtered to remove metal salt byproducts. The resulting solution may be reacted with $SiRH_3$, wherein R is phenyl, tolyl, or other appropriate aryl substituent. The resulting mixture may be purified by fractional distillation. Exemplary hydrocarbon solutions suitable for these synthesis methods include diethyl ether, pentane, hexane, or toluene. All of the starting materials are commercially available.

Exemplary alpha-haloamidinate precursors include:

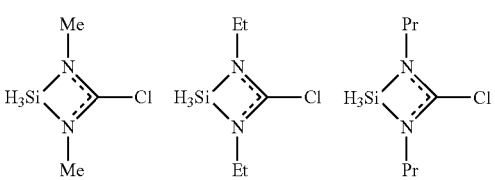

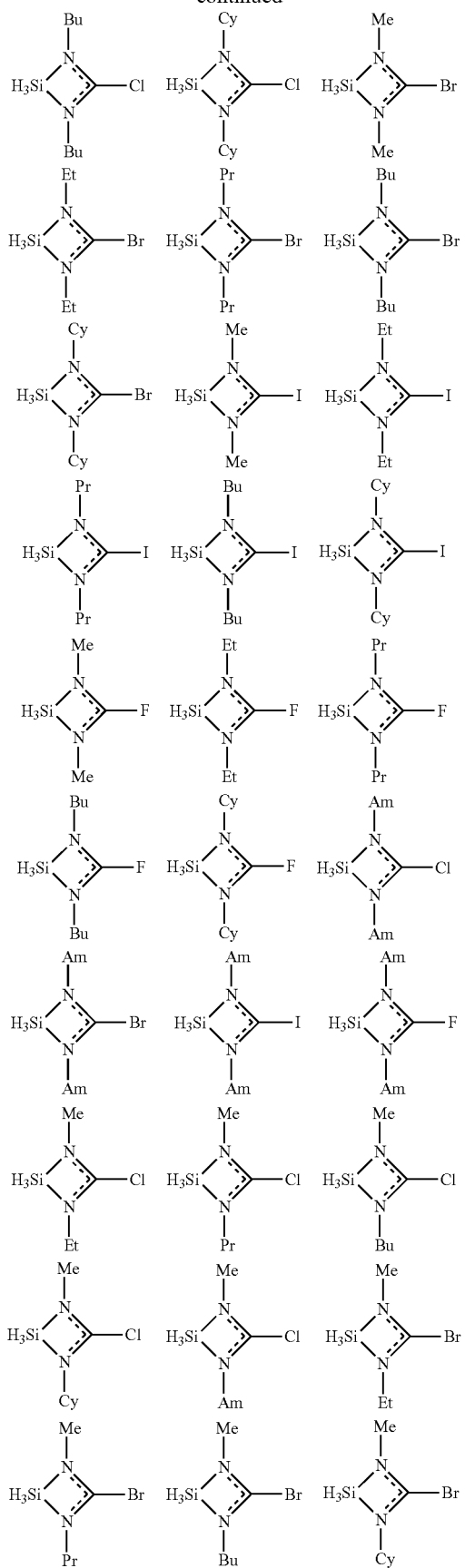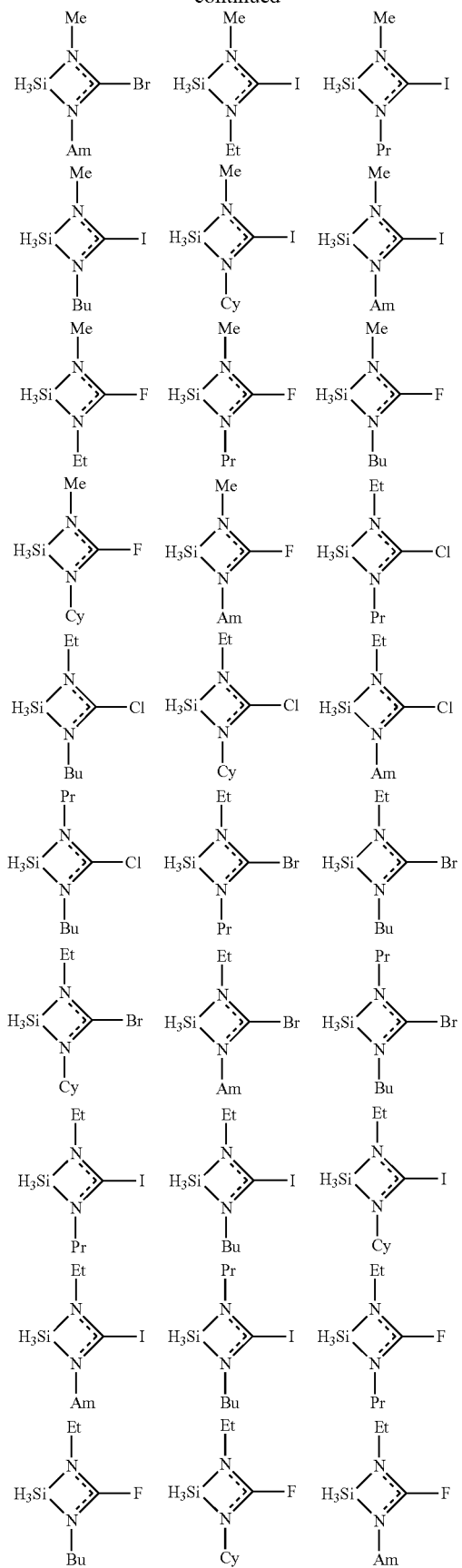

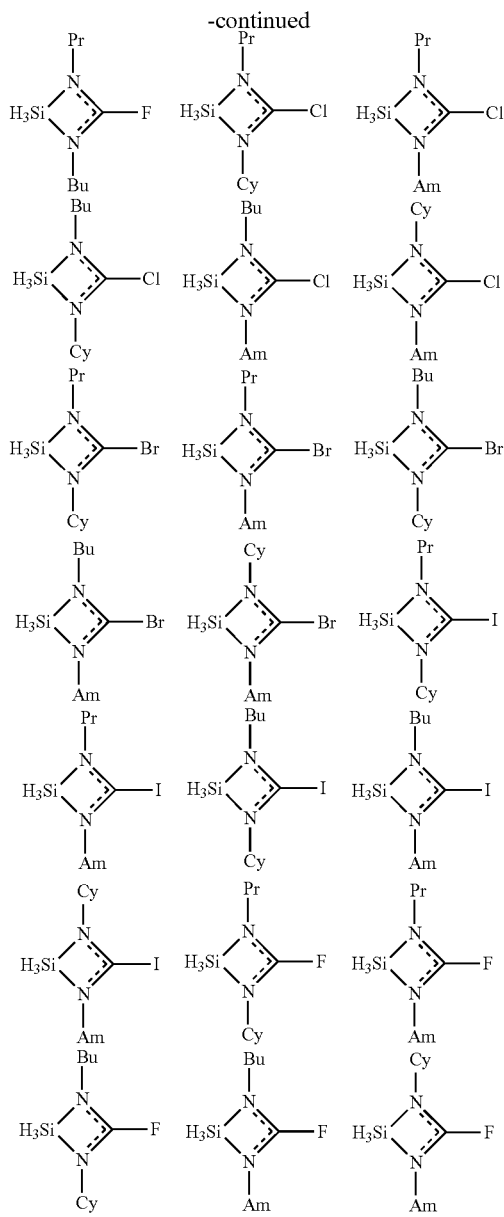

Preferably, the alpha-haloamidinate is H$_3$Si(-(iPr)N—C(Cl)—N(iPr)—).

Also disclosed are methods of using the disclosed organosilane precursors for vapor deposition methods. The disclosed methods provide for the use of the organosilane precursors for deposition of silicon-containing films. The disclosed methods may be useful in the manufacture of semiconductor, photovoltaic, LCD-TFT, or flat panel type devices. The method includes: providing a substrate; providing a vapor including at least one of the disclosed organosilane precursors: and contacting the vapor with the substrate (and typically directing the vapor to the substrate) to form a silicon-containing layer on at least one surface of the substrate.

The disclosed methods also provide for forming a bimetal-containing layer on a substrate using a vapor deposition process and, more particularly, for deposition of SiMO$_x$ films wherein x is 4 and M is Ta, Hf, Nb, Mg, Al, Sr, Y, Ba, Ca, As, Sb, Bi, Sn, Pb, Co, lanthanides (such as Er), or combinations thereof. The disclosed methods may be useful in the manufacture of semiconductor, photovoltaic, LCD-TFT, or flat panel type devices. The method includes: providing a substrate; providing a vapor including at least one of the disclosed organosilane precursors and contacting the vapor with the substrate (and typically directing the vapor to the substrate) to form a bi metal-containing layer on at least one surface of the substrate. An oxygen source, such as O$_3$, O$_2$, H$_2$O, NO, H$_2$O$_2$, acetic acid, formalin, para-formaldehyde, oxygen radicals thereof, and combinations thereof, but preferably O$_3$ or plasma treated O$_2$ may also be provided with the vapor.

The disclosed organosilane precursors may be used to deposit silicon-containing films using any deposition methods known to those of skill in the art. Examples of suitable deposition methods include without limitation, conventional chemical vapor deposition (CVD), low pressure chemical vapor deposition (LPCVD), atomic layer deposition (ALD), pulsed chemical vapor deposition (P-CVD), thermal ALD, thermal CVD, plasma enhanced atomic layer deposition (PE-ALD), plasma enhanced chemical vapor deposition (PE-CVD), spatial ALD, or combinations thereof. Preferably, the deposition method is ALD, spatial ALD, or PE-ALD.

The vapor of the organosilane precursor is introduced into a reaction chamber containing at least one substrate. The temperature and the pressure within the reaction chamber and the temperature of the substrate are held at conditions suitable for vapor deposition of at least part of the organosilane precursor onto the substrate. In other words, after introduction of the vaporized precursor into the chamber, conditions within the chamber are such that at least part of the vaporized precursor is deposited onto the substrate to form the silicon-containing film. A co-reactant may also be used to help in formation of the Si-containing layer.

The reaction chamber may be any enclosure or chamber of a device in which deposition methods take place, such as, without limitation, a parallel-plate type reactor, a cold-wall type reactor, a hot-wall type reactor, a single-wafer reactor, a multi-wafer reactor, or other such types of deposition systems. All of these exemplary reaction chambers are capable of serving as an ALD reaction chamber. The reaction chamber may be maintained at a pressure ranging from about 0.5 mTorr to about 20 Torr. In addition, the temperature within the reaction chamber may range from about 20° C. to about 600° C. One of ordinary skill in the art will recognize that the temperature may be optimized through mere experimentation to achieve the desired result.

The temperature of the reactor may be controlled by either controlling the temperature of the substrate holder or controlling the temperature of the reactor wall. Devices used to heat the substrate are known in the art. The reactor wall is heated to a sufficient temperature to obtain the desired film at a sufficient growth rate and with desired physical state and composition. A non-limiting exemplary temperature range to which the reactor wall may be heated includes from approximately 20° C. to approximately 600° C. When a plasma deposition process is utilized, the deposition temperature may range from approximately 20° C. to approximately 550° C. Alternatively, when a thermal process is performed, the deposition temperature may range from approximately 300° C. to approximately 600° C.

Alternatively, the substrate may be heated to a sufficient temperature to obtain the desired silicon-containing film at a sufficient growth rate and with desired physical state and composition. A non-limiting exemplary temperature range to which the substrate may be heated includes from 150° C. to 600° C. Preferably, the temperature of the substrate remains less than or equal to 500° C.

The type of substrate upon which the silicon-containing film will be deposited will vary depending on the final use intended. In some embodiments, the substrate may be a patterned photoresist film made of hydrogenated carbon, for example $CH_x$, wherein x is greater than zero. In some embodiments, the substrate may be chosen from oxides which are used as dielectric materials in MIM, DRAM, or FeRam technologies (for example, $ZrO_2$ based materials, $HfO_2$ based materials, $TiO_2$ based materials, rare earth oxide based materials, ternary oxide based materials, etc.) or from nitride-based films (for example, TaN) that are used as an oxygen barrier between copper and the low-k layer. Other substrates may be used in the manufacture of semiconductors, photovoltaics, LCD-TFT, or flat panel devices. Examples of such substrates include, but are not limited to, solid substrates such as metal nitride containing substrates (for example, TaN, TiN, WN, TaCN, TiCN, TaSiN, and TiSiN); insulators (for example, $SiO_2$, $Si_3N_4$, SiON, $HfO_2$, $Ta_2O_5$, $ZrO_2$, $TiO_2$, $Al_2O_3$, and barium strontium titanate); or other substrates that include any number of combinations of these materials. The actual substrate utilized may also depend upon the specific precursor embodiment utilized. In many instances though, the preferred substrate utilized will be selected from hydrogenated carbon, TiN, SRO, Ru, and Si type substrates, such as polysilicon or crystalline silicon substrates.

The disclosed organosilane precursors may be supplied either in neat form or in a blend with a suitable solvent, such as toluene, ethyl benzene, xylene, mesitylene, decane, dodecane, octane, hexane, pentane, tertiary amines, acetone, tetrahydrofuran, ethanol, ethylmethylketone, 1,4-dioxane, or others. The disclosed precursors may be present in varying concentrations in the solvent. For example, the resulting concentration may range from approximately 0.05 M to approximately 2 M.

The neat or blended organosilane precursors are introduced into a reactor in vapor form by conventional means, such as tubing and/or flow meters. The precursor in vapor form may be produced by vaporizing the neat or blended precursor solution through a conventional vaporization step such as direct vaporization, distillation, by bubbling, or by using a sublimator such as the one disclosed in PCT Publication WO2009/087609 to Xu et al. The neat or blended precursor may be fed in liquid state to a vaporizer where it is vaporized before it is introduced into the reactor. Alternatively, the neat or blended precursor may be vaporized by passing a carrier gas into a container containing the precursor or by bubbling the carrier gas into the precursor. The carrier gas may include, but is not limited to, Ar, He, or $N_2$, and mixtures thereof. Bubbling with a carrier gas may also remove any dissolved oxygen present in the neat or blended precursor solution. The carrier gas and precursor are then introduced into the reactor as a vapor.

If necessary, the container may be heated to a temperature that permits the organosilane precursor to be in its liquid phase and to have a sufficient vapor pressure. The container may be maintained at temperatures in the range of, for example, 0-150° C. Those skilled in the art recognize that the temperature of the container may be adjusted in a known manner to control the amount of organosilane precursor vaporized.

In addition to the disclosed precursor, a reaction gas may also be introduced into the reactor. The reaction gas may be an oxidizing agent such as one of $O_2$; $O_3$; $H_2O$; $H_2O_2$; oxygen containing radicals such as O. or OH.; NO; $NO_2$; carboxylic acids such as formic acid, acetic acid, propionic acid; radical species of NO, $NO_2$, or the carboxylic acids; para-formaldehyde; and mixtures thereof. Preferably, the oxidizing agent is selected from the group consisting of $O_2$, $O_3$, $H_2O$, $H_2O_2$, oxygen containing radicals thereof such as O. or OH., and mixtures thereof. Preferably, when an ALD process is performed, the co-reactant is plasma treated oxygen, ozone, or combinations thereof. When an oxidizing gas is used, the resulting silicon containing film will also contain oxygen.

Alternatively, the reaction gas may be a reducing agent such as one of $H_2$, $NH_3$, $(SiH_3)_3N$, hydridosilanes (such as $SiH_4$, $Si_2H_6$, $Si_3H_8$, $Si_4H_{10}$, $Si_5H_{10}$, $Si_6H_{12}$), chlorosilanes and chloropolysilanes (such as $SiHCl_3$, $SiH_2Cl_2$, $SiH_3Cl$, $Si_2Cl_6$, $Si_2HCl_5$, $Si_3Cl_8$), alkylsilanes (such as $(CH_3)_2SiH_2$, $(C_2H_5)_2SiH_2$, $(CH_3)SiH_3$, $(C_2H_5)SiH_3$), hydrazines (such as $N_2H_4$, MeHNNH$_2$, MeHNNHMe), organic amines (such as $N(CH_3)H_2$, $N(C_2H_5)H_2$, $N(CH_3)_2H$, $N(C_2H_5)_2H$, $N(CH_3)_3$, $N(C_2H_5)_3$, $(SiMe_3)_2NH)$, pyrazoline, pyridine, B-containing molecules (such as $B_2H_6$, 9-borabicyclo[3,3,1]none, trimethylboron, triethylboron, borazine), alkyl metals (such as trimethylaluminum, triethylaluminum, dimethylzinc, diethylzinc), radical species thereof, and mixtures thereof. Preferably, the reducing agent is $H_2$, $NH_3$, $SiH_4$, $Si_2H_6$, $Si_3H_8$, $SiH_2Me_2$, $SiH_2Et_2$, $N(SiH_3)_3$, hydrogen radicals thereof, or mixtures thereof. When a reducing agent is used, the resulting silicon containing film may be pure Si.

The reaction gas may be treated by a plasma, in order to decompose the reaction gas into its radical form. $N_2$ may also be utilized as a reducing agent when treated with plasma. For instance, the plasma may be generated with a power ranging from about 50 W to about 500 W, preferably from about 100 W to about 200 W. The plasma may be generated or present within the reactor itself. Alternatively, the plasma may generally be at a location removed from the reactor, for instance, in a remotely located plasma system. One of skill in the art will recognize methods and apparatus suitable for such plasma treatment.

The disclosed organosilane precursors may also be used with a halosilane or polyhalodisilane, such as hexachlorodisilane pentachlorodisilane, or tetrachlorodisilane, and one or more co-reactant gases to form SiN or SiCN films, as disclosed in PCT Publication Number WO2011/123792, the entire contents of which are incorporated herein in their entireties.

When the desired silicon-containing film also contains another element, such as, for example and without limitation, Ta, Hf, Nb, Mg, Al, Sr, Y, Ba, Ca, As, Sb, Bi, Sn, Pb, Co, lanthanides (such as Er), or combinations thereof, the co-reactants may include a metal-containing precursor which is selected from, but not limited to, metal alkyls, such as $Ln(RCp)_3$ or $Co(RCp)_2$, metal amines, such as $Nb(Cp)(Nt-Bu)(NMe_2)_3$ and any combination thereof.

The organosilane precursor and one or more co-reactants may be introduced into the reaction chamber simultaneously (chemical vapor deposition), sequentially (atomic layer deposition), or in other combinations. For example, the organosilane precursor may be introduced in one pulse and two additional metal sources may be introduced together in a separate pulse [modified atomic layer deposition]. Alternatively, the reaction chamber may already contain the co-reactant prior to introduction of the organosilane precursor. The co-reactant may be passed through a plasma system localized or remotely from the reaction chamber, and decomposed to radicals. Alternatively, the organosilane precursor may be introduced to the reaction chamber continuously while other metal sources are introduced by pulse (pulsed-chemical vapor deposition). In each example, a pulse may be followed by a purge or evacuation step to remove excess amounts of the component introduced. In each example, the pulse may last for a time period ranging from about 0.01 s to about 10 s, alternatively from about 0.3 s to about 3 s, alternatively from about 0.5 s to about 2 s. In another alternative, the organosilane precursor and one or more co-reactants may be simultaneously sprayed from a shower head under which a susceptor holding several wafers is spun (spatial ALD).

In one non-limiting exemplary atomic layer deposition type process, the vapor phase of an organosilane precursor is introduced into the reaction chamber, where it is contacted with a suitable substrate. Excess organosilane precursor may then be removed from the reaction chamber by purging and/or evacuating the reaction chamber. An oxygen source is introduced into the reaction chamber where it reacts with the absorbed organosilane precursor in a self-limiting manner. Any excess oxygen source is removed from the reaction chamber by purging and/or evacuating the reaction chamber. If the desired film is a silicon oxide film, this two-step process may provide the desired film thickness or may be repeated until a film having the necessary thickness has been obtained.

Alternatively, if the desired film is a silicon metal oxide film (i.e., $SiMO_x$, wherein x may be 4 and M is Ta, Hf, Nb, Mg, Al, Sr, Y, Ba, Ca, As, Sb, Bi, Sn, Pb, Co, lanthanides (such as Er), or combinations thereof), the two-step process above may be followed by introduction of a second vapor of a metal-containing precursor into the reaction chamber. The metal-containing precursor will be selected based on the nature of the silicon metal oxide film being deposited. After introduction into the reaction chamber, the metal-containing precursor is contacted with the substrate. Any excess metal-containing precursor is removed from the reaction chamber by purging and/or evacuating the reaction chamber. Once again, an oxygen source may be introduced into the reaction chamber to react with the metal-containing precursor. Excess oxygen source is removed from the reaction chamber by purging and/or evacuating the reaction chamber. If a desired film thickness has been achieved, the process may be terminated. However, if a thicker film is desired, the entire four-step process may be repeated. By alternating the provision of the organosilane precursor, metal-containing precursor, and oxygen source, a film of desired composition and thickness can be deposited.

Additionally, by varying the number of pulses, films having a desired stoichiometric M:Si ratio may be obtained. For example, a $SiMO_2$ film may be obtained by having one pulse of the organosilane precursor and one pulses of the metal-containing precursor, with each pulse being followed by pulses of the oxygen source. However, one of ordinary skill in the art will recognize that the number of pulses required to obtain the desired film may not be identical to the stoichiometric ratio of the resulting film.

In another alternative, Si or dense SiCN films may be deposited via an ALD or modified ALD process using the disclosed compounds and a halosilane compound having the formula $Si_aH_{2a+2-b}X_b$, wherein X is F, Cl, Br, or I; a=1 through 6; and b=1 through (2a+2); or a cyclic halosilane compound having the formula $—Si_cH_{2c-d}X_d—$, wherein X is F, Cl, Br, or I; c=3-8; and d=1 through 2c. Preferably the halosilane compound is trichlorosilane, hexachlorodisilane (HCDS), pentachlorodisilane (PODS), tetrachlorodisilane, or hexachlorocyclohexasilane. One of ordinary skill in the art will recognize that the Cl in these compounds may be substituted by Br or I when lower deposition temperatures are necessary, due to the lower bond energy in the Si—X bond (i.e., Si—Cl=456 kJ/mol; Si—Br=343 kJ/mol; Si—I=339 kJ/mol). If necessary, the deposition may further utilize an N-containing co-reactant, such as $NH_3$. Vapors of the disclosed precursors and the halosilane compounds may be introduced sequentially or simultaneously into the reactor, depending on the desired concentration of the final film. The selected sequence of precursor injection will be determined based upon the desired film composition targeted. The precursor introduction steps may be repeated until the deposited layer achieves a suitable thickness. One of ordinary skill in the art will recognize that the introductory pulses may be simultaneous when using a spatial ALD device. As described in PCT Pub No WO2011/123792, the order of the introduction of the precursors may be varied and the deposition may be performed with or without the $NH_3$ co-reactant in order to tune the amounts of carbon and nitrogen in the SiCN film.

The silicon-containing films resulting from the processes discussed above may include Si, $SiO_2$, SiN, SiON, SiCN, SiCOH, or $MSiO_x$, wherein M is an element such as Hf, Zr, Ti, Nb, Ta, or Ge, and x may be 4, depending of course on the oxidation state of M. One of ordinary skill in the art will recognize that by judicial selection of the appropriate organosilane precursor and co-reactants, the desired film composition may be obtained.

Upon obtaining a desired film thickness, the film may be subject to further processing, such as thermal annealing, furnace-annealing, rapid thermal annealing, UV or e-beam curing, and/or plasma gas exposure. Those skilled in the art recognize the systems and methods utilized to perform these additional processing steps. For example, the silicon-containing film may be exposed to a temperature ranging from approximately 200° C. and approximately 1000° C. for a time ranging from approximately 0.1 second to approximately 7200 seconds under an inert atmosphere, a H-containing atmosphere, a N-containing atmosphere, an O-containing atmosphere, or combinations thereof. Most preferably, the temperature is 600° C. for less than 3600 seconds under a H-containing atmosphere. The resulting film may contain fewer impurities and therefore may have improved performance characteristics. The annealing step may be performed in the same reaction chamber in which the deposition process is performed. Alternatively, the substrate may be removed from the reaction chamber, with the annealing/flash annealing process being performed in a separate apparatus. Any of the above post-treatment methods, but especially thermal annealing, has been found effective to reduce carbon and nitrogen contamination of the silicon-containing film.

EXAMPLES

The following non-limiting examples are provided to further illustrate embodiments of the invention. However, the examples are not intended to be all inclusive and are not intended to limit the scope of the inventions described herein.

Example 1

Synthesis of $SiH_3(N^iPr\text{-amd})$

With stirring, a diethyl ether solution of methyl lithium (91 mL, 1.6M, 0.146 mol) is slowly added to a 40° C. solution of N,N'-diisopropylcarbodiimide (22.5 mL, 0.145 mol) in diethyl ether (150 mL). After the addition is completed, the resulting colorless suspension is allowed to warm to room temperature and stirred for three hours to form a colorless solution. A separate flask is equipped with a −78° C. (dry ice/acetone) condenser, charged with diethyl ether (100 mL) and cooled to −78° C. With stirring, monochlorosilane (13.2 g, 0.198 mol) is slowly condensed into the second flask, followed by slow addition of lithium amidinate solution from the first step. Initially some fuming was observed followed by formation of a colorless precipitate. After completing the addition, the suspension was brought to room temperature slowly with vigorous stirring overnight. The suspension is filtered over a medium glass frit containing a pad of Celite and the resulting colorless solution distilled at atmospheric pressure using Vigreux column to remove solvent. The receiving flask is replaced and cooled in −78° C. bath, the desired product is distilled at 25-28° C./200-300 mTorr as a colorless liquid. Yield: 7.9 g (31.6%). FIG. 1 is a TGA graph demonstrating the percentage of weight loss with temperature change for this precursor as compared to that of DiPAS. $^{29}$Si NMR (80 MHz, C$_6$D$_6$, 25° C.) δ (ppm)=−87.7; $^1$H NMR (400 MHz, C$_6$D$_6$, 25° C.) δ (ppm)=4.73 (s, 3H, SiH$_3$), 3.38 (sept., 2H, $^1J_{H-H}$=8.0 Hz, NCH(CH$_3$)$_2$), 1.40 (s, 3H, CCH$_3$), 1.12 (d, 12H, $^1J_{H-H}$=8.0 Hz, NCH(CH$_3$)$_2$).

Example 2

Synthesis of SiH$_3$(N$^t$Bu-amd)

A flask is equipped with a −78° C. (dry ice/acetone) condenser, charged with diethyl ether (100 mL) and cooled to −78° C. With stirring, monochlorosilane (8.9 g, 0.134 mol) is slowly condensed into the flask. In a second flask, a diethyl ether solution of methyl lithium (101 mL, 1.6M, 0.162 mol) is slowly added to a −40° C. solution of N,N'-di-tertbutylcarbodiimide (25 g, 0.162 mol) in diethyl ether (100 mL). After the addition is completed, the resulting colorless suspension of lithium amidinate is allowed to warm to room temperature and stirred for one hour to form a colorless solution. The resulting Li-amd solution is cooled to 0° C. and added by cannula to the −78° C. solution of monochlorosilane (MCS) in diethyl ether. Initially some fuming was observed followed by the formation of a colorless precipitate. After completing the addition, the suspension was brought to room temperature with vigorous stirring.

The stirring was stopped and solids allowed to settle before filtration over a medium glass frit with a bed of Celite. The resulting colorless solution is transferred to a flask containing dried Amberlyst A21 Resin (5 g), stirred slightly and left to stand at room temperature for 14 hours. The solution is then filtered and distilled at atmospheric pressure using a short path column to remove solvent and high volatiles to afford a highly viscous pale yellow liquid. The receiving flask is replaced and cooled to −78° C., the desired product is distilled at 55-61° C./100 mTorr as a colorless liquid which slowly crystallized upon standing at room temperature. Yield: 14.5 g (54.1%). MP=36° C., $^{29}$Si NMR (80 MHz, C$_6$D$_6$, 25° C.) δ (ppm)=−117.5; $^1$H NMR (400 MHz, C$_6$D$_6$, 25° C.) δ (ppm)= 5.05 (s, 3H, SiH$_3$), 1.79 (s, 3H, CCH$_3$), 1.25 (s, 9H, NC(CH$_3$)$_3$).

Example 3

ALD of SiH$_3$(N$^i$Pr-amd)

Figure 2:
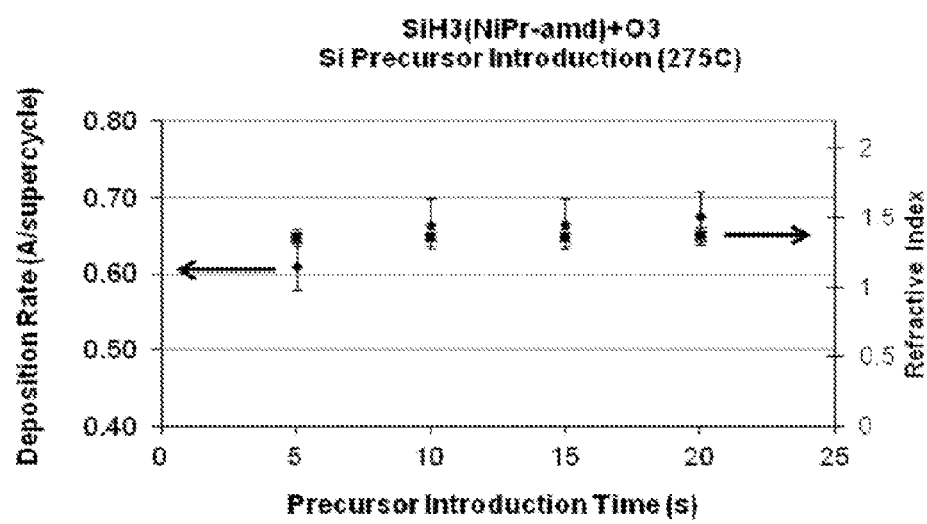
FIG. 2 is a graph demonstrating precursor introduction time versus deposition rate and refractive index.

ALD tests were performed using the SiH$_3$(N$^i$Pr-amd) prepared in Example 1, which was placed in a vessel at room temperature. Typical ALD conditions were used, such as using ozone with a reactor pressure fixed at ~0.5 Torr. As shown in FIG. 2, ALD behavior with complete surface saturation and reaction was assessed at 275° C. on pure silicon wafers. One of ordinary skill in the art will recognize that different deposition equipment may exhibit surface saturation at different precursor introduction times. The refractive index is characteristic of SiO$_2$ film (pure SiO$_2$ has a refractive index of 1.46). Changes in the refractive index due to changes in precursor introduction time are indicative of impurities in the film.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

What is claimed is:

1. A Si-containing thin film forming precursor having the following formula:

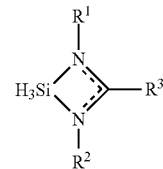

wherein R$^1$ and R$^2$ may each independently be H, a C1 to C6 alkyl group, or a C3-C20 aryl or heterocycle group and R$^3$ may be H, a C1 to C6 alkyl group, a C3-C20 aryl or heterocycle group, an amino group, an alkoxy group, or a halogen.

2. The Si-containing thin film forming precursor of claim 1, having the following formula:

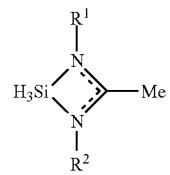

wherein R$^1$ and R$^2$ may each independently be a C1 to C6 alkyl group.

3. The Si-containing thin film forming precursor of claim 2, wherein the molecule is SiH$_3$(N$^i$Pr-amd).

4. The Si-containing thin film forming precursor of claim 1, having the following formula:

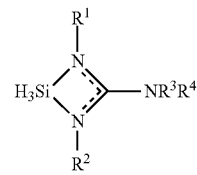

wherein R$^1$, R$^2$, R$^3$ and R$^4$ may each independently be H, a C1 to C6 alkyl group, or a C3-C20 aryl or heterocycle.

5. The Si-containing thin film forming precursor of claim 1, having the following formula:

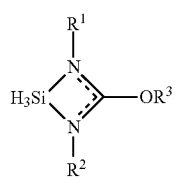

wherein $R^1$, $R^2$, and $R^3$ may each independently be H, a C1 to C6 alkyl group, or a C3-C20 aryl or heterocycle.

6. The Si-containing thin film forming precursor of claim 1, having the following formula:

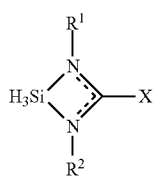

wherein $R^1$ and $R^2$ may each independently be H, a C1 to C6 alkyl group, or a C3-C20 aryl or heterocycle and X may be Cl, Br, I, or F.

7. A method of depositing a Si-containing layer on a substrate, the method comprising:
Introducing at least one organosilane precursor of claim 1 into a reactor having at least one substrate disposed therein;
depositing at least part of the organosilane precursor onto the at least one substrate to form a Si-containing layer using a vapor deposition method.

8. The method of claim 7, further comprising introducing into the reactor at least one co-reactant.

9. The method of claim 8, wherein the co-reactant is selected from the group consisting of $P_2$, $O_3$, $H_2O$, $H_2O_2$, NO, $NO_2$, a carboxylic acid, radicals thereof, and combinations thereof, preferably plasma treated oxygen or ozone.

10. The method of claim 8, wherein the co-reactant is selected from the group consisting of $H_2$, $NH_3$, $(SiH_3)_3N$, hydridosilanes (such as $SiH_4$, $Si_2H_6$, $Si_3H_8$, $Si_4H_{10}$, $Si_5H_{10}$, $Si_6H_{12}$), chlorosilanes and chloropolysilanes (such as $SiHCl_3$, $SiH_2Cl_2$, $SiH_3Cl$, $Si_2Cl_6$, $Si_2HCl_5$, $Si_3Cl_8$), alkysilanes (such as $Me_2SiH_2$, $Et_2SiH_2$, $MeSiH_3$, $EtSiH_3$), hydrazines (such as $N_2H_4$, $MeHNNH_2$, $MeHNNHMe$), organic amines (such as $NMeH_2$, $NEtH_2$, $NMe_2H$, $NEt_2H$, $NMe_3$, $NEt_3$, $(SiMe_3)_2NH$), pyrazoline, pyridine, B-containing molecules (such as $B_2H_6$, 9-borabicylo[3,3,1]none, trimethylboron, triethylboron, borazine), alkyl metals (such as trimethylaluminum, triethylaluminum, dimethylzinc, diethylzinc), radical species thereof, and mixtures thereof.

11. The method of claim 10, wherein the co-reactant is selected from the group consisting of $H_2$, $NH_3$, $SiH_4$, $Si_2H_6$, $Si_3H_8$, $SiH_2Me_2$, $SiH_2Et_2$, $N(SiH_3)_3$, hydrogen radicals thereof, and mixtures thereof.

12. The method of claim 10, wherein the co-reactant is selected from the group consisting of $SiHCl_3$, $Si_2Cl_6$, $Si_2HCl_5$, $Si_2H_2Cl_4$, and cyclo-$Si_6H_6Cl_6$.

13. The method of claim 7, wherein the vapor deposition process is a chemical vapor deposition process.

14. The method of claim 7, wherein the vapor deposition process is an atomic layer deposition process.

15. The method of claim 7, wherein the organosilane precursor has the following formula:

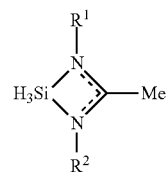

wherein $R^1$ and $R^2$ may each independently be a C1 to C6 alkyl group.

16. The method of claim 15, wherein the organosilane precursor is $SiH_3(N^iPr\text{-amd})$.

17. The method of claim 7, wherein the organosilane precursor has the following formula:

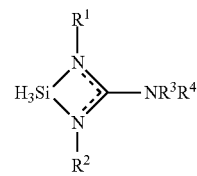

wherein $R^1$, $R^2$, $R^3$ and $R^4$ may each independently be H, a C1 to C6 alkyl group, or a C3-C20 aryl or heterocycle.

18. The method of claim 7, wherein the organosilane precursor has the following formula:

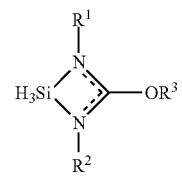

wherein $R^1$, $R^2$, and $R^3$ may each independently be H, a C1 to C6 alkyl group, or a C3-C20 aryl or heterocycle.

19. The method of claim 7, wherein the organosilane precursor has the following formula:

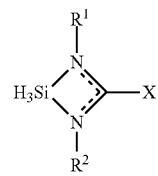

wherein $R^1$ and $R^2$ may each independently be H, a C1 to C6 alkyl group, or a C3-C20 aryl or heterocycle and X may be Cl, Br, I, or F.

* * * * *